(12) United States Patent
Lo et al.

(10) Patent No.: US 11,447,829 B2
(45) Date of Patent: Sep. 20, 2022

(54) NUCLEIC ACID REARRANGEMENT AND INTEGRATION ANALYSIS

(71) Applicant: GRAIL, LLC, Menlo Park, CA (US)

(72) Inventors: Yuk-Ming Dennis Lo, Hong Kong (CN); Rossa Wai Kwun Chiu, Hong Kong (CN); Kwan Chee Chan, Hong Kong (CN); Peiyong Jiang, Hong Kong (CN); Wai Kei Lam, Hong Kong (CN); Haiqiang Zhang, Hong Kong (CN)

(73) Assignee: GRAIL, LLC, Menlo Park, CA (US)

( * ) Notice: Subject to any disclaimer, the term of this patent is extended or adjusted under 35 U.S.C. 154(b) by 325 days.

(21) Appl. No.: 16/456,354

(22) Filed: Jun. 28, 2019

(65) Prior Publication Data

US 2020/0002770 A1    Jan. 2, 2020

Related U.S. Application Data

(60) Provisional application No. 62/691,890, filed on Jun. 29, 2018.

(51) Int. Cl.
| | |
|---|---|
| *C12P 19/34* | (2006.01) |
| *C12Q 1/6886* | (2018.01) |
| *C12Q 1/70* | (2006.01) |
| *G16B 30/10* | (2019.01) |

(52) U.S. Cl.
CPC ........... *C12Q 1/6886* (2013.01); *C12Q 1/701* (2013.01); *G16B 30/10* (2019.02); *C12Q 2600/158* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 8,722,334 B2 | 5/2014 | Lo et al. | |
| 9,121,069 B2 | 9/2015 | Lo et al. | |
| 9,469,876 B2 | 10/2016 | Kuslich et al. | |
| 2013/0310263 A1* | 11/2013 | Lo ....................... | C12Q 1/6809 506/2 |
| 2016/0002723 A1 | 1/2016 | Menchen et al. | |

(Continued)

FOREIGN PATENT DOCUMENTS

WO    WO-2020006370 A1    1/2020

OTHER PUBLICATIONS

Akagi, K. et al. Genome-wide analysis of HPV integration in human cancers reveals recurrent, focal genomic instability. Genome Res. 24:185-199 (2014).

(Continued)

*Primary Examiner* — Kenneth R Horlick
(74) *Attorney, Agent, or Firm* — Greenberg Traurig, LLP

(57) ABSTRACT

Provided herein are methods and systems for identifying chimeric nucleic acid fragments, e.g., organism-pathogen chimeric nucleic acid fragments and chromosomal rearrangement chimeric nucleic acid fragments. Also provided herein are methods and systems relating to determining a pathogen integration profile or a chromosomal rearrangement in a biological sample and determining a classification of pathology based at least in part on a pathogen integration profile or a chromosomal rearrangement in a biological sample. In certain aspects of the present disclosure, cell-free nucleic acid molecules from a biological sample are analyzed.

24 Claims, 14 Drawing Sheets

(56) References Cited

U.S. PATENT DOCUMENTS

2016/0292356 A1 10/2016 Kim et al.
2017/0275691 A1 9/2017 Christians et al.

OTHER PUBLICATIONS

Campitelli, M. Human Papillomavirus Mutational Insertion: Specific Marker of Circulating Tumor DNA in Cervical Cancer Patients. PLOS ONE, 7(8):e43393:1-5 (Aug. 2012).

Capone, R.B. et al. Detection and Quantitation of Human Papillomavirus (HPV) DNA in the Sera of Patients with HPV-associated Head and Neck Squamous Cell Carcinoma. Clinical Cancer Research, Nov. 2000;6(11):4171-5.

Chan, K.C. Allen, et al. Cell-free nucleic acids in plasma, serum and urine: a new tool in molecular diagnosis. Ann. Clin. Biochem 40:122-130(2003).

Chandrani, P. et al. NGS-based approach to determine the presence of HPV and their sites of integration in human cancer genome. British Journal of Cancer 112:1958-1965 (Jun. 9, 2015).

Chen, Y. et al. Viral Carcinogenesis: Factors Inducing DNA Damage and Virus Integration. Cancers 6(4), 2155-2186 (2014).

Cooper, G.M. The Cell: A Molecular Approach. 2nd edition. Sunderland (MA): Sinauer Associates; 2000: pp. 1-5. Tumor Viruses. Available from: https://www.ncbi.nlm.nih.gov/books/NBK9929/.

Desgarges, S. and Ciuffi, A. (2012) Viral Integration and Consequences on Host Gene Expression. In: Witzany G. (eds) Viruses: Essential Agents of Life. Springer, Dordrecht. pp. 147-175.

Dong, S.M. et al. Detection and quantitation of human papillomavirus DNA in the plasma of patients with cervical carcinoma. Cancer Epidemiol Biomarkers Prev 11: 3-6 (2002).

Khoury, J.D. et al. Landscape of DNA Virus Associations across Human Malignant Cancers: Analysis of 3,775 Cases Using RNA-Seq. Journal of Virology, 87(16):8916-8926 (Aug. 2013).

Kraus, I. et al. The majority of viral-cellular fusion transcripts in cervical carcinomas cotranscribe cellular sequences of known or predicted genes. Cancer Research 68(7): 2514-2522 (Apr. 1, 2008).

Leary, et al. Detection of chromosomal alterations in the circulation of cancer patients with whole-genome sequencing. Sci Transl Med. Nov. 28, 2012;4(162):162ra154.

Leary, et al. Development of personalized tumor biomarkers using massively parallel sequencing. Sci Transl Med. Feb. 24, 2010;2(20):20ra14.

Liu, V.W. et al. Low incidence of HPV DNA in sera of pretreatment cervical cancer patients. Gynecol Oncol 82: 269-272 (2001).

Luo, G.G. et al. Oncogenic viruses and cancer. Virol Sin. Apr. 2015; 30(2): 83-84.

Mesri, E.A. et al. Human Viral Oncogenesis: A Cancer Hallmarks Analysis. Cell Host & Microbe, 15(3):266-282 (Mar. 12, 2014).

Miao Xu et al., "Genome-wide profiling of Epstein-Barr virus integration by targeted sequencing in Epstein-Barr virus associated malignancies", Theranostics 2019, vol. 9, Issue 4, pp. 1115-1124.

Nguyen, Nam-Phuong D. et al. ViFi: accurate detection of viral integration and mRNA fusion reveals indiscriminate and unregulated transcription in proximal genomic regions in cervical cancer. Nucleic Acids Research, Mar. 20, 2018; 46(7):3309-3325.

Ojesina, A.I. et al. Landscape of genomic alterations in cervical carcinomas. Nature. 2014;506(488):371-375 (Feb. 20, 2014).

Parfenov, M. et al. Characterization of HPV and host genome interactions in primary head and neck cancers. Proc Natl Acad Sci USA. 111:15544-15549 (2014).

PCT/US19/39750 Internationals Search Report and Written Opinion dated Oct. 31, 2019.

Popescu, N.C. et al. Preferential sites for viral integration on mammalian genome. Cancer Genet Cytogenet. Oct. 15, 1989;42(2):157-71.

Pornthanakasem, W. et al. Human papillomavirus DNA in plasma of patients with cervical cancer. BMC Cancer 1:2(1-8) 2001.

Rizzo, G. et al. Defining the genomic landscape of head and neck cancers through nextgeneration sequencing. Oral Diseases, 21(1):e11-e24 (Jan. 2015).

Schmidt, H. et al. A liquid biopsy for head and neck cancers. Expert Review of Molecular Diagnostics 16(2):165-172 (Jan. 18, 2016).

Schmitz, Martina et al. Non-Random Integration of the HPV Genome in Cervical Cancer. PLOS ONE, 7(6):e39632:1-10 (Jun. 27, 2012).

Shimada, T. et al. Human papillomavirus DNA in plasma of patients with HPV16 DNA-positive uterine cervical cancer. Jpn J Clin Oncol 40: 420-424 (2010).

Sung, W.K. et al. Genome-wide survey of recurrent HBV integration in hepatocellular carcinoma. Nat Genet. May 27, 2012;44(7):765-9.

Tang, K.W. et al. The landscape of viral expression and host gene fusion and adaptation in human cancer. Nature Communications, 4(2513):1-9 (Oct. 2013).

Thorland, E.C. et al. Common fragile sites are preferential targets for HPV16 integrations in cervical tumors. Oncogene. Feb. 27, 2003;22(8):1225-37.

Tseng, C.J. et al. Detection of human papillomavirus types 16 and 18 mRNA in peripheral blood of advanced cervical cancer patients and its association with prognosis. J Clin Oncol 17: 1391-1396 (1999).

Tu, T. et al. HBV DNA Integration: Molecular Mechanisms and Clinical Implications. Viruses, 9(4):75:1-18(2017).

Tuna, Musaffe et al. Next Generation sequencing and its applications in HPV-associated cancers. Oncotarget, 8(5):8877-8889 (2017).

Valouev, Anton et al. Discovery of recurrent structural variants in nasopharyngeal carcinoma. Genome Research, 24:300-309 (2014).

Wagner, Steffen et al. Human Papillomavirus-Related Head and Neck Cancer. Oncology Research and Treatment 40:334-340 (May 19, 2017).

Wentzensen, N. et al. Systematic review of genomic integration sites of human papillomavirus genomes in epithelial dysplasia and invasive cancer of the female lower genital tract. Cancer Res. Jun. 1, 2004;64(11):3878-84.

Williams, Vonetta M et al. HPV-DNA Integration and Carcinogenesis: Putative Roles for Inflammation and Oxidative Stress. Future virology 6.1 (2011): 45-57. PMC. Web. Jun. 1, 2018.

Xu, B. et al. Multiplex Identification of Human Papillomavirus 16 DNA Integration Sites in Cervical Carcinomas. PLoS One, 8(6):e66693:1-18 (Jun. 2013).

Yang, H.J. et al. Quantification of human papillomavirus DNA in the plasma of patients with cervical cancer. Int J Gynecol Cancer 14: 903-910 (2004).

Zhao, X. et al. Dr.VIS: a database of human disease-related viral integration sites. Nucleic Acids Res. Jan. 2012; 40(Database issue): D1041-D1046 (Published Online Dec. 1, 2011).

Huang et al., "Analysis of microbial sequences in plasma cell-free DNA for early-onset breast cancer patients and healthy females," *BMC Medical Genomics*, 11(Suppl 1):16 (2018).

Lau et al., "Viral-human chimeric transcript predisposes risk to liver cancer development and progression," *Cancer Cell*, 25(3):335-349 (2014).

Tennakoon et al., "BATVI: Fast, sensitive and accurate detection of virus integrations," *BMC Bioinformatics*, 17(Suppl 3):71 (2017).

\* cited by examiner

Type A fragment
Read 1
Mapped to pathogen
genome, *e.g.*, HPV genome
Read 2
Mapped to host organism
genome, *e.g.*, human genome
Type B fragment
Read 1
Partly mapped to pathogen
genome, *e.g.*, HPV genome
Read 2
Mapped to host organism
genome, *e.g.*, human genome
HPV
sequence
Human
sequence
FIG. 2

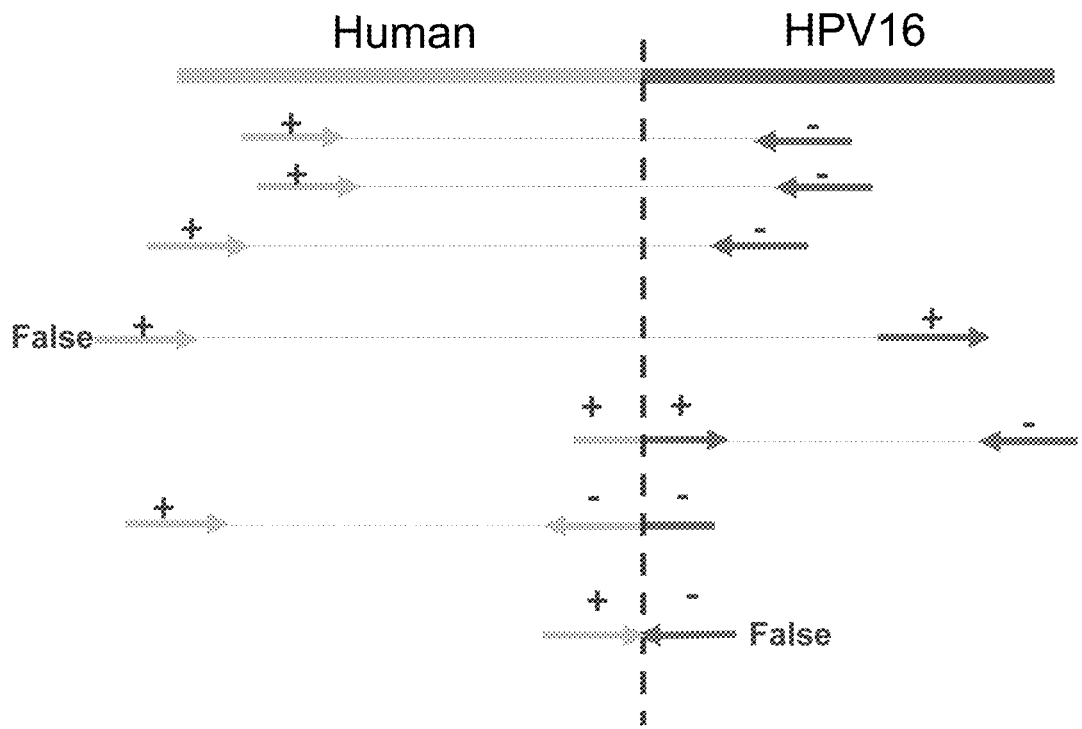

| Type A human-HPV fragment read pair | | Expected strand of Human-HPV chimeric read | Relative location of break point to human sequence | Relative location of break point to HPV sequence |
|---|---|---|---|---|
| Strand of read mapped to human genome | Strand of read mapped to HPV genome | | | |
| + | + | +- or -+ | Downstream | Downstream |
| + | - | ++ or -- | Downstream | Upstream |
| - | + | -- or ++ | Upstream | Downstream |
| - | - | -+ or +- | Upstream | Upstream |

FIG. 4

| Sample Type | Sample ID | Total no. of candidate regions | Without diversity score filtering || Diversity score ≥ 4 || No. of PCR assays designed | No. of targeted breakpoint for validation | No. of breakpoints validated |
|---|---|---|---|---|---|---|---|---|---|
| | | | No. of chimeric reads | No. of breakpoints | No. of chimeric reads | No. of breakpoints | | | |
| CaCx | 3485 | 458 | 28317 | 1054 | 10723 | 6 | 8 | 6 | 1 |
| | C-788 | 43 | 77 | 26 | 0 | 0 | - | - | - |
| | C-801 | 2 | 0 | 0 | 0 | 0 | - | - | - |
| | C-819 | 2 | 0 | 0 | 0 | 0 | - | - | - |
| | C-822 | 5 | 0 | 0 | 0 | 0 | - | - | - |
| | C-877 | 9 | 0 | 0 | 0 | 0 | - | - | - |
| HNSCC | TBR_1019 | 8 | 0 | 0 | 0 | 0 | - | - | - |
| | TBR1245 | 1 | 0 | 0 | 0 | 0 | - | - | - |
| | TBR1988 | 3 | 0 | 0 | 0 | 0 | - | - | - |
| | TBR1989 | 12414 | 234667 | 96039 | 1521 | 41 | 10 | 9 | 3 |
| | TBR2175 | 22 | 9 | 3 | 0 | 0 | - | - | - |

FIG. 12

| Sample Type | Disease Stage | Sample ID | No. of Candidate regions | Without diversity score filtering | | Diversity score ≥ 4 | | After merging breakpoint with close genomic coordinates | No. of PCR assays designed | No. of targeted breakpoint for validation | No. of breakpoints validated |
|---|---|---|---|---|---|---|---|---|---|---|---|
| | | | | No. of chimeric reads | No. of breakpoints | No. of Chimeric reads | No. of break points | | | | |
| HNSCC | III | TBR2175 | 1544 | 44970 | 1428 | 3399 | 31 | 23 | 17 | 14 | 13 |
| | I | TBR1245 | 485 | 7614 | 447 | 1483 | 22 | 17 | 12 | 7 | 7 |
| | III | TBR1019 | 889 | 27380 | 1344 | 34 | 2 | 2 | 2 | 1 | 1 |
| | III | TBR1989 | 1339 | 12960 | 1115 | 15 | 1 | 1 | 1 | 1 | 1 |
| | I | TBR2002 | 48 | 10 | 2 | 0 | 0 | - | - | - | - |
| | III | TBR1067 | 0 | 0 | 0 | 0 | 0 | - | - | - | - |
| | I | TBR1988 | 0 | 0 | 0 | 0 | 0 | - | - | - | - |

FIG. 13

NUCLEIC ACID REARRANGEMENT AND INTEGRATION ANALYSIS

CROSS-REFERENCE

This application claims the benefit of U.S. Provisional Application No. 62/691,890, filed Jun. 29, 2018, which application is incorporated herein by reference in its entirety.

BACKGROUND

Many diseases and conditions can be associated with a chromosomal rearrangement or integration of a pathogen (e.g., virus) nucleic acid into a host organism (e.g., human) genome. For example, an inter- and intrachromosomal rearrangement, such as a translocation, can be associated with cancer. Furthermore, viruses can be associated with about 20% of human cancer cases, and about 70% of cervical cancers and precancerous cervical lesions can be caused by infection of two human papilloma virus (HPV) types (16 and 18). Currently, for most solid tumours, chromosomal rearrangement or pathogen integration is mainly detected using tumor tissue specimen acquired through tissue biopsy, which may involve a large needle, an endoscope, or open surgery—and can be invasive, risky, costly, and painful. There is a need for improved methods, systems, and computer readable medium for identifying chromosomal rearrangements and nucleic acid integration events using, e.g., cell-free nucleic acid molecules from biological samples.

SUMMARY

Described herein, in one aspect, is a method of analyzing a biological sample of an organism to determine a classification of pathology, the method comprising: (a) analyzing a plurality of cell-free nucleic acid molecules from the biological sample to identify an organism-pathogen chimeric nucleic acid fragment, wherein analyzing each of the plurality of cell-free nucleic acid molecules comprises: identifying a first end of the respective cell-free nucleic acid molecule as being from a first genome, identifying a second end of the respective cell-free nucleic acid molecule as being from a second genome, and identifying the organism-pathogen chimeric nucleic acid fragment when the first genome is a genome of a pathogen and the second genome is a genome of the organism, wherein the organism and pathogen are different; and (b) determining a classification of pathology based at least in part on the organism-pathogen chimeric nucleic acid fragment. In some cases, the identifying the first end as being from the first genome comprises obtaining a sequence read of the respective cell-free nucleic acid molecule and aligning at least a portion of a first end of the sequence read to a reference genome of the pathogen. In some cases, the identifying the second end as being from the second genome comprises obtaining a sequence read of the respective cell-free nucleic acid molecule and aligning at least a portion of a second end of the sequence read to a reference genome of the organism. In some cases, the analyzing each of the plurality of cell-free nucleic acid molecules comprises obtaining a sequence read of the respective cell-free nucleic acid molecule and identifying the organism-pathogen chimeric nucleic acid fragment when at least a portion of a first end of the sequence read aligns to a reference genome of a pathogen and at least a portion of a second end of the sequence read aligns to a reference genome of the organism. In some embodiments, the method further comprises obtaining sequence reads of the plurality of cell-free nucleic acid molecules by paired-end sequencing, and wherein the paired-end sequencing generates a pair of sequence reads for each of the plurality of cell-free nucleic acid molecules. In some cases, the pair of sequence reads comprises a first sequence read of a first end of the respective cell-free nucleic acid molecule and a second sequence read of a second end of the respective cell-free nucleic acid molecule. In some cases, the identifying the organism-pathogen chimeric nucleic acid fragment comprises aligning the first sequence read, or a portion thereof, to a reference genome of a pathogen and aligning the second sequence read, or a portion thereof, to a reference genome of the organism. In some cases, the identifying the organism-pathogen chimeric nucleic acid fragment comprises aligning at least 20, 25, 30, 35, 40, 45, 50, 55, 60, 65, 70, 75, 80, 85, 90, 95, or 100 consecutive nucleotides of the first sequence read to the reference genome of the pathogen and aligning at least 20, 25, 30, 35, 40, 45, 50, 55, 60, 65, 70, 75, 80, 85, 90, 95, or 100 consecutive nucleotides of the second sequence read to the reference genome of the organism. In some cases, the identifying the organism-pathogen chimeric nucleic acid fragment comprises aligning at least 50 consecutive nucleotides of the first sequence read to the reference genome of the pathogen and aligning at least 50 consecutive nucleotides of the second sequence read to the reference genome of the organism. In some cases, the method further comprises determining a pathogen integration index based on an amount of organism-pathogen chimeric nucleic acid fragments from the biological sample; and determining the classification of the pathology based at least in part on the pathogen integration index. In some cases, the determining the pathogen integration index comprises determining an amount of the plurality of cell-free nucleic molecules that comprise a first end from the genome of the pathogen and a second end from the genome of the pathogen. In some cases, the determining the pathogen integration index comprises comparing the amount of the organism-pathogen chimeric nucleic acid fragments to an amount of the plurality of cell-free nucleic acid molecules comprising a first end from the genome of the pathogen and a second end from the genome of the pathogen. In some cases, the comparing comprises determining a ratio of the amount of the organism-pathogen chimeric nucleic acid fragments to the amount of the plurality of cell-free nucleic acid molecules comprising a first end from the genome of the pathogen and a second end from the genome of the pathogen. In some cases, the identifying the organism-pathogen chimeric nucleic acid fragment further comprises analyzing amplification reactions of the plurality of cell-free nucleic acid molecules from the biological sample. In some cases, the amplification reactions comprise a first primer complementary to a first target sequence in the genome of the pathogen and a second primer complementary to a second target sequence in the genome of the organism. In some cases, the amplification reactions comprise polymerase chain reaction (PCR). In some cases, the method further comprises analyzing sequences of amplicons generated by the amplification reactions. In some cases, the pathogen comprises a virus. In some cases, the virus comprises Epstein-Barr Virus DNA, human papillomavirus DNA, Hepatitis B Virus DNA, Hepatitis C Virus nucleic acids, or fragments thereof. In some cases, the virus is human papillomavirus. In some cases, the classification of pathology comprises a presence of a cancer. In some cases, the cancer is selected from the group consisting of bladder cancer, bone cancer, a brain tumor, breast cancer, carcinoma of cervix, colorectal cancer, esophageal cancer, gastrointestinal cancer, hematopoietic malignancy, head and neck squamous cell carcinoma, leukemia, liver cancer, lung cancer, lymphoma, myeloma, nasal cancer, nasopharyngeal cancer, oral cancer, oropharyngeal cancer, ovarian cancer, prostate cancer, sarcoma, stomach cancer, and thyroid cancer. In some cases, the classification of pathology comprises a type of cancer. In some cases, the type of cancer comprises carcinoma of cervix or head and neck squamous cell carcinoma. In some cases, the plurality of cell-free nucleic acid molecules comprise deoxyribonucleic acid molecules. In some cases, the organism is an animal. In some cases, the animal is a mammal. In some cases, the mammal is a human. In some cases, the biological sample is plasma, serum, or urine. In some cases, the biological sample is plasma. In some cases, the analyzing the plurality of cell-free nucleic acid molecules from the biological sample is performed by a computer system.

Described herein, in one aspect, is a method of identifying an organism-pathogen chimeric cell-free nucleic fragment from a biological sample of an organism, the method comprising: (a) determining a first end of a cell-free nucleic acid molecule as being from a first genome and a second end of the cell-free nucleic acid molecule as being from a second genome; and (b) identifying the organism-pathogen cell-free nucleic acid fragment when the first genome is a genome of a pathogen and the second genome is a genome of the organism, wherein the organism and pathogen are different.

In some cases, the determining the first end as being from the first genome comprises obtaining a sequence read of the cell-free nucleic acid molecule and aligning at least a portion of a first end of the sequence read to a reference genome of the pathogen. In some cases, the determining the second end as being from the second genome comprises obtaining a sequence read of the cell-free nucleic acid molecule and aligning at least a portion of a second end of the sequence read to a reference genome of the organism. In some cases, the method further comprises obtaining a sequence read of the cell-free nucleic acid molecule and identifying the organism-pathogen chimeric nucleic acid fragment when at least a portion of a first end of the sequence read aligns to a reference genome of a pathogen and at least a portion of a second end of the sequence read aligns to a reference genome of the organism. In some cases, the method further comprises obtaining sequence reads of the cell-free nucleic acid molecule by paired-end sequencing, and wherein the paired-end sequencing generates a pair of sequence reads for the of cell-free nucleic acid molecule. In some cases, the pair of sequence reads comprises a first sequence read of a first end of the cell-free nucleic acid molecule and a second sequence read of a second end of the cell-free nucleic acid molecule. In some cases, the identifying the organism-pathogen chimeric nucleic acid fragment comprises aligning the first sequence read, or a portion thereof, to a reference genome of the pathogen and aligning the second sequence read, or a portion thereof, to a reference genome of the organism. In some cases, the identifying the organism-pathogen chimeric nucleic acid fragment comprises aligning at least 20, 25, 30, 35, 40, 45, 50, 55, 60, 65, 70, 75, 80, 85, 90, 95, or 100 consecutive nucleotides of the first sequence read to the reference genome of the pathogen and aligning at least 20, 25, 30, 35, 40, 45, 50, 55, 60, 65, 70, 75, 80, 85, 90, 95, or 100 consecutive nucleotides of the second sequence read to the reference genome of the organism. In some cases, the identifying the organism-pathogen chimeric nucleic acid fragment comprises aligning at least 50 consecutive nucleotides of the first sequence read to the reference genome of the pathogen and aligning at least 50 consecutive nucleotides of the second sequence read to the reference genome of the organism. In some cases, the identifying the organism-pathogen chimeric nucleic acid fragment further comprises analyzing amplification reactions of the cell-free nucleic acid molecules from the biological sample. In some cases, the amplification reactions comprise a first primer complementary to a first target sequence in the genome of the pathogen and a second primer complementary to a second target sequence in the genome of the organism. In some cases, the amplification reactions comprise polymerase chain reaction (PCR). In some cases, the method further comprises analyzing sequences of amplicons generated by the amplification reactions. In some cases, the pathogen comprises a virus. In some cases, the virus comprises Epstein-Barr Virus DNA, human papillomavirus DNA, Hepatitis B Virus DNA, Hepatitis C Virus nucleic acids, or fragments thereof. In some cases, the virus is human papillomavirus. In some cases, the cell-free nucleic acid molecule is deoxyribonucleic acid. In some cases, the organism is an animal. In some cases, the animal is a mammal. In some cases, the mammal is a human. In some cases, the biological sample is plasma, serum, or urine. In some cases, the biological sample is plasma. In some cases, the determining the first end of the cell-free nucleic acid molecule as being from the first genome and the second end of the cell-free nucleic acid molecule as being from the second genome is performed by a computer system.

Described herein, in one aspect, is a method of analyzing cell-free nucleic acid molecules from a biological sample of an organism to determine a type of pathology, the method comprising: (a) analyzing cell-free nucleic acid molecules from the biological sample to determine a pathogen integration profile, the pathogen integration profile comprising a position of a breakpoint in a genome of a pathogen that integrates in a genome of the organism; and (b) determining the type of pathology based on the pathogen integration profile.

In some cases, the pathogen integration profile is determined by detecting an organism-pathogen chimeric nucleic acid fragment in a cell-free nucleic acid molecule from the biological sample when the cell-free nucleic acid molecule comprises genomic sequence from the pathogen and genomic sequence from the organism. In some cases, the detecting comprises identifying a first end of the cell-free nucleic acid molecule as being from a genome of the pathogen, and identifying a second end of the cell-free nucleic acid molecule as being from a genome of the organism. In some cases, the detecting comprises obtaining sequence reads from the cell-free nucleic acid molecules from the biological sample, and analyzing the sequence reads to detect the organism-pathogen chimeric nucleic acid fragment. In some cases, the sequence reads are obtained by paired-end sequencing of the cell-free nucleic acid molecules, and wherein the paired-end sequencing generates a pair of sequences reads for each of the cell-free nucleic acid molecules. In some cases, the pair of sequence reads comprises a first sequence read of a first end of the respective cell-free nucleic acid molecule and a second sequence read of a second end of the respective cell-free nucleic acid molecule. In some cases, the detecting the organism-pathogen chimeric nucleic acid fragment comprises aligning at least 20, 25, 30, 35, 40, 45, 50, 55, 60, 65, 70, 75, 80, 85, 90, 95, or 100 consecutive nucleotides of the first sequence read to a reference genome of the pathogen and aligning at least 20, 25, 30, 35, 40, 45, 50, 55, 60, 65, 70, 75, 80, 85, 90, 95, or 100 consecutive nucleotides of a second sequence read to a reference genome of the organism. In some cases, the determining the pathogen integration profile further comprises: determining a pathogen integration index based on an amount of organism-pathogen chimeric nucleic acid fragments. In some cases, the detecting the organism-pathogen chimeric nucleic acid fragment comprises analyzing amplification reactions of the cell-free nucleic acid molecules from the biological sample. In some cases, the amplification reactions comprise a first primer complementary to a first target sequence in the genome of the pathogen, and a second primer complementary to a second target sequence in the genome of the organism. In some cases, the amplification reactions comprise polymerase chain reaction (PCR). In some cases, the method further comprises analyzing sequences of amplicons generated by the amplification reactions. In some cases, the pathogen comprises a virus. In some cases, the virus comprises Epstein-Barr Virus DNA, human papillomavirus DNA, Hepatitis B Virus DNA, Hepatitis C Virus nucleic acids, or fragments thereof. In some cases, the virus is human papillomavirus. In some cases, the classification of pathology comprises a type of cancer. In some cases, the type of cancer comprises carcinoma of cervix or head and neck squamous cell carcinoma. In some cases, the cell-free nucleic acid molecules comprise deoxyribonucleic acid molecules. In some cases, the organism is an animal. In some cases, the animal is a mammal. In some cases, the mammal is a human. In some cases, the biological sample is plasma, serum, or urine. In some cases, the biological sample is plasma. In some cases, the analyzing the cell-free nucleic acid molecules is performed by a computer system.

Described herein, in one aspect, is a method of analyzing cell-free nucleic acid molecules from a biological sample of an organism to determine a pathogen integration profile, the method comprising analyzing cell-free nucleic acid molecules from the biological sample to determine a pathogen integration profile, the pathogen integration profile comprising a position of an integration breakpoint in a genome of a pathogen that integrates in a genome of the organism.

In some cases, the pathogen integration profile is determined by detecting an organism-pathogen chimeric nucleic acid fragment in a cell-free nucleic acid molecule from the biological sample when the cell-free nucleic acid molecule comprises genomic sequence from the pathogen and genomic sequence from the organism. In some cases, the detecting comprises identifying a first end of the cell-free nucleic acid molecule as being from a genome of the pathogen, and identifying a second end of the cell-free nucleic acid molecule as being from a genome of the organism. In some cases, the detecting comprises obtaining sequence reads from the cell-free nucleic acid molecules from the biological sample, and analyzing the sequence reads to detect the organism-pathogen chimeric nucleic acid fragment. In some cases, the sequence reads are obtained by paired-end sequencing of the cell-free nucleic acid molecules, and wherein the paired-end sequencing generates a pair of sequences reads for each of the cell-free nucleic acid molecules. In some cases, the pair of sequence reads comprises a first sequence read of a first end of the respective cell-free nucleic acid molecule and a second sequence read of a second end of the respective cell-free nucleic acid molecule. In some cases, the detecting the organism-pathogen chimeric nucleic acid fragment comprises aligning at least 20, 25, 30, 35, 40, 45, 50, 55, 60, 65, 70, 75, 80, 85, 90, 95, or 100 consecutive nucleotides of the first sequence read to a reference genome of the pathogen and aligning at least 20, 25, 30, 35, 40, 45, 50, 55, 60, 65, 70, 75, 80, 85, 90, 95, or 100 consecutive nucleotides of a second sequence read to a reference genome of the organism. In some cases, the determining the pathogen integration profile further comprises: determining a pathogen integration index based on an amount of organism-pathogen chimeric nucleic acid fragments. In some cases, the detecting the organism-pathogen chimeric nucleic acid fragment comprises analyzing amplification reactions of the cell-free nucleic acid molecules from the biological sample. In some cases, the amplification reactions comprise a first primer complementary to a first target sequence in the genome of the pathogen, and a second primer complementary to a second target sequence in the genome of the organism. In some cases, the amplification reactions comprise polymerase chain reaction (PCR). In some cases, the method further comprises analyzing sequences of amplicons generated by the amplification reactions. In some cases, the pathogen comprises a virus. In some cases, the virus comprises Epstein-Barr Virus DNA, human papillomavirus DNA, Hepatitis B Virus DNA, Hepatitis C Virus nucleic acids, or fragments thereof. In some cases, the virus is human papillomavirus. In some cases, the cell-free nucleic acid molecules comprise deoxyribonucleic acid molecules. In some cases, the organism is an animal. In some cases, the animal is a mammal. In some cases, the mammal is a human. In some cases, the biological sample is plasma, serum, or urine. In some cases, the biological sample is plasma. In some cases, the analyzing the cell-free nucleic acid molecules is performed by a computer system. In some cases, the analyzing comprises sequencing the cell-free nucleic acid molecules. In some cases, the analyzing comprises: identifying sequence reads of cell-free nucleic acid molecules from the biological sample comprising a same potential integration breakpoint; and detecting the integration breakpoint based on the sequence reads. In some cases, the detecting the integration breakpoint based on the sequence reads comprises: assessing a variability in lengths of sequences of each of the sequence reads aligning to a genomic region flanking the potential integration breakpoint; and based on the assessing, detecting the integration breakpoint in the organism. In some cases, the analyzing comprises: identifying sequence read pairs of cell-free nucleic acid molecules from the biological sample comprising a same potential integration breakpoint; and detecting the integration breakpoint based on the sequence read pairs. In some cases, the detecting the integration breakpoint based on the sequence read pairs comprises: determining a strand orientation of a first sequence read and a second sequence read of each of the sequence read pairs; filtering out a sequence read pair comprising a strand orientation of the first sequence read and the second sequence read inconsistent with a strand orientation of the first sequence read and the second sequence read of a majority of the sequence read pairs; and after the filtering out, detecting the integration breakpoint based on the sequence read pairs.

In some cases, the detecting the integration breakpoint based on the sequence read pairs comprises: assessing a variability in lengths of sequences of sequence reads of the sequence read pairs aligning to a genomic region flanking the potential integration breakpoint; and based on the assessing, detecting the integration breakpoint. In some cases, the identifying the sequence read pairs comprises: identifying organism-pathogen chimeric sequence read pairs generated from paired-end sequencing of the cell-free nucleic acid molecules from the biological sample that comprise a first sequence read aligning to a reference genome of the organism and a second sequence read aligning to a reference genome of the pathogen, thereby identifying Type A organism-pathogen chimeric sequence read pairs; grouping, from the Type A organism-pathogen chimeric sequence read pairs, Type A organism-pathogen chimeric sequence read pairs comprising first sequence reads that are overlapping or separated within a predetermined distance in the reference genome of the organism, and second sequence reads that are overlapping or separated within a predetermined distance in the reference genome of the pathogen, thereby identifying an organism-pathogen candidate integration region in the reference genomes of the organism and the pathogen; and identifying organism-pathogen chimeric sequence read pairs generated from paired-end sequencing of the cell-free nucleic acid molecules from the biological sample that comprise a first sequence read aligning to the organism-pathogen candidate integration region and a second sequence read comprising a first sequence aligning to the reference genome of the organism and a second sequence aligning to the reference genome of the pathogen, thereby identifying Type B organism-pathogen chimeric sequence read pairs. In some cases, the predetermined distance is at most 10, at most 50, at most 75, at most 100, at most 120, at most 150, at most 175, at most 200, at most 225, at most 250, at most 275, at most 300 at most 325, at most 350, at most 375, at most 400, at most 425, at most 450, at most 475, or at most 500 bases. In some cases, in the organism-pathogen candidate integration region, there are at least 3, 4, 5, 6, 7, 8, 9, 10, 11, 12, 15, 20, 50, 100, 200, 1000, 10,000, 50,000, 100,000, or more Type A organism-pathogen chimeric sequence read pairs. In some cases, the detecting the integration breakpoint comprises: determining a strand orientation of the first sequence read and the second sequence read of each of the Type A organism-pathogen chimeric sequence read pairs and the Type B organism-pathogen chimeric sequence read pairs; filtering out, from the Type B organism-pathogen chimeric sequence read pairs, Type B organism-pathogen chimeric sequence read pairs that have a strand orientation of the first sequence read and the second sequence read inconsistent with the strand orientation of the first sequence read and the second sequence read of a majority of the Type A organism-pathogen chimeric sequence read pairs within the organism-pathogen candidate integration region; and after the filtering out, detecting the integration breakpoint based on the Type B organism-pathogen chimeric sequence read pairs. In some cases, the detecting the integration breakpoint comprises: determining a Diversity Score for the Type B organism-pathogen chimeric sequence read pairs; wherein the Diversity Score is calculated as $$\frac{\sigma1 + \sigma2}{\max\left(\frac{\sigma1}{\sigma2}, \frac{\sigma2}{\sigma1}\right)},$$

wherein σ1 is a standard deviation of lengths of the first sequences of the Type B organism-pathogen chimeric sequence read pairs aligning to the reference genome of the organism, and wherein σ2 is a standard deviation of lengths of the second sequences of the Type B organism-pathogen chimeric sequence read pairs aligning to the reference genome of the pathogen; and detecting the integration breakpoint based on the Type B organism-pathogen chimeric sequence read pairs, if the Diversity Score is equal to or higher than a predetermined cutoff value. In some cases, the predetermined cutoff value is at least 1, at least 1.6, at least 2.0, at least 2.4, at least 2.8, at least 3.0, at least 3.4, at least 3.8, at least 4.0, at least 4.2, at least 4.4, at least 4.6, at least 4.8, at least 5.0, at least 5.4, at least 5.8, at least 6.0, at least 6.5, at least 7.0, at least 8, at least 9, at least 10, at least 20, at least 50, or at least 100.

Described herein, in one aspect, is a method of analyzing a biological sample of an organism to detect a chromosomal rearrangement, the method comprising: identifying sequence reads of cell-free nucleic acid molecules from the biological sample comprising sequence of a same potential chromosomal rearrangement; assessing a variability in lengths of sequences of each of the sequence reads aligning to a genomic region flanking the potential chromosomal rearrangement; and based on the assessing, detecting the chromosomal rearrangement in the organism.

In some cases, the organism is a human. In some cases, the chromosomal rearrangement comprises a chromosome translocation, chromosome deletion, chromosome inversion, or chromosome amplification. In some cases, the identifying the sequence reads comprises: identifying chromosomal chimeric sequence read pairs generated from paired-end sequencing of the cell-free nucleic acid molecules from the biological samples and comprising a sequence read comprising the potential chromosomal rearrangement. In some cases, the identifying the chromosomal chimeric sequence read pairs comprises: identifying chromosomal chimeric sequence read pairs generated from the paired-end sequencing that comprise a first sequence read aligning to a first genomic region of a reference genome of the organism, and a second sequence read aligning to a second genomic region of the reference genome, thereby identifying Type A chromosomal chimeric sequence read pairs, wherein a relative positioning of the first genomic region and second genomic region in the reference genome is indicative of the potential chromosomal rearrangement; grouping, from the Type A chromosomal chimeric sequence read pairs, Type A chromosomal chimeric sequence read pairs comprising first sequence reads that are overlapping or separated within a predetermined distance in the first genomic region and comprising second sequence reads that are overlapping or separated within a predetermined distance in the second genomic region, thereby identifying a candidate rearrangement region in the first genomic region and the second genomic region; and identifying chromosomal chimeric sequence read pairs generated from the paired-end sequencing that comprise a first sequence read aligning to the candidate integration region and a second sequence read comprising a first sequence aligning to the first genomic region and a second sequence aligning to the second genomic region, thereby identifying Type B chromosomal chimeric sequence read pairs. In some cases, the assessing the variability comprises: determining a Diversity Score for the Type B chromosomal chimeric sequence read pairs, wherein the Diversity Score is calculated as $$\frac{\sigma1 + \sigma2}{\max\left(\frac{\sigma1}{\sigma2}, \frac{\sigma2}{\sigma1}\right)},$$

wherein σ1 is a standard deviation of lengths of the first sequences of the Type B chromosomal chimeric sequence read pairs aligning to the first genomic region, and wherein σ2 is a standard deviation of lengths of the first sequences of the Type B chromosomal chimeric sequence read pairs aligning to the second genomic region. In some cases, the detecting the chromosomal rearrangement comprises detecting the chromosomal rearrangement based on the Type B chromosomal chimeric sequence read pairs, if the Diversity Score is equal to or higher than a predetermined cutoff value. In some cases, the predetermined cutoff value is at least 1, at least 1.6, at least 2.0, at least 2.4, at least 2.8, at least 3.0, at least 3.4, at least 3.8, at least 4.0, at least 4.2, at least 4.4, at least 4.6, at least 4.8, at least 5.0, at least 5.4, at least 5.8, at least 6.0, at least 6.5, at least 7.0, at least 8, at least 9, at least 10, at least 20, at least 50, or at least 100. In some cases, a distance between the first genomic region and the second genomic region is at least 140 bases, at least 180 bases, at least 250 bases, at least 350 bases, at least 450 bases, at least 550 bases, at least 750 bases, at least 900 bases, at least 1100 bases, at least 1250 bases, at least 1800 bases, at least 2500 bases, at least 3500 bases, at least 5500 bases, at least 7500 bases, at least 9000 bases, or at least $10^4$ bases. In some cases, a relative 5' to 3' relationship of the first genomic region and the second genomic region in the reference genome is opposite to a relative 5' to 3' relationship of the first sequence read and the second sequence read in the respective cell-free nucleic acid molecule of each of the Type A chromosomal chimeric sequence read pairs.

Described herein, in one aspect, is a method of analyzing a biological sample of an organism to detect a chromosomal rearrangement, the method comprising: identifying sequence read pairs of cell-free nucleic acid molecules from the biological sample comprising a same potential chromosomal rearrangement; determining a strand orientation of a first sequence read and a second sequence read of each of the sequence read pairs; filtering out a sequence read pair comprising a strand orientation of the first sequence read and the second sequence read inconsistent with a strand orientation of the first sequence read and the second sequence read of a majority of the sequence read pairs; and after the filtering out, detecting the chromosomal rearrangement in the organism based on the sequence read pairs.

In some cases, the organism is a human. In some cases, the chromosomal rearrangement comprises a chromosome translocation, chromosome deletion, chromosome inversion, or chromosome amplification. In some cases, the identifying the sequence read pairs comprises: identifying chromosomal chimeric sequence read pairs generated from paired-end sequencing of the cell-free nucleic acid molecules from the biological sample that comprise a first sequence read aligning to a first genomic region of a reference genome of the organism, and a second sequence read aligning to a second genomic region of the reference genome, thereby identifying Type A chromosomal chimeric sequence read pairs, wherein a relative positioning of the first genomic region and second genomic region in the reference genome is indicative of the potential chromosomal rearrangement; grouping, from the Type A chromosomal chimeric sequence read pairs, Type A chromosomal chimeric sequence read pairs comprising first sequence reads that are overlapping or separated within a predetermined distance in the first genomic region, and second sequence reads that are overlapping or separated within a predetermined distance in the second genomic region, thereby identifying a candidate rearrangement region in the first genomic region and the second genomic region; and identifying chromosomal chimeric sequence read pairs generated from paired-end sequencing of the cell-free nucleic acid molecules from the biological sample that comprise a first sequence read aligning to the candidate rearrangement region and a second sequence read comprising a first sequence aligning to the first genomic region and a second sequence aligning to the second genomic region, thereby identifying Type B chromosomal chimeric sequence read pairs. In some cases, the filtering out comprises: filtering out Type B chromosomal chimeric sequence read pairs that have a strand orientation of the first sequence read and the second sequence read inconsistent with the strand orientation of the first sequence read and the second sequence read of a majority of the Type A chromosomal chimeric sequence read pairs within the candidate rearrangement region. In some cases, a distance between the first genomic region and the second genomic region is at least 140 bases, at least 180 bases, at least 250 bases, at least 350 bases, at least 450 bases, at least 550 bases, at least 750 bases, at least 900 bases, at least 1100 bases, at least 1250 bases, at least 1800 bases, at least 2500 bases, at least 3500 bases, at least 5500 bases, at least 7500 bases, at least 9000 bases, or at least $10^4$ bases. In some cases, a relative 5' to 3' relationship of the first genomic region and the second genomic region in the reference genome is opposite to a relative 5' to 3' relationship of the first sequence read and the second sequence read in the respective cell-free nucleic acid molecule of each of the Type A chromosomal chimeric sequence read pairs.

Described herein, in one aspect, is a method comprising determining a classification of pathology based at least in part on the chromosomal rearrangement that is determined by any method described herein.

Described herein, in one aspect, is a computer system comprising one or more processors and a non-transitory computer readable medium comprising instructions operable, when executed by the one or more computer processors, to cause the computer system to perform any method described herein.

Described herein, in one aspect, is a non-transitory computer-readable medium comprising instructions operable, when executed by one or more processors of a computer system, to cause the computer system to perform any method described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features described herein are set forth with particularity in the appended claims. A better understanding of the features and advantages described herein will be obtained by reference to the following detailed description that sets forth illustrative embodiments, in which the principles described herein are utilized, and the accompanying drawings of which:

FIG. 2 is a schematic illustrating pairs of sequences reads generated by paired-end sequencing from two types of nucleic acid fragments, Type A and Type B.

FIG. 4 shows a schematic and a chart demonstrating an exemplary strandedness-based filtration process.

FIG. 12 shows a table summarizing viral DNA integration analysis by an exemplary algorithm on plasma sample from patients with cervical cancer (CaCx), head and neck squamous cell carcinoma (HNSCC).

FIG. 13 shows a table summarizing viral DNA integration analysis by an exemplary algorithm on tumor tissue samples from patients with head and neck squamous cell carcinoma (HNSCC).

DETAILED DESCRIPTION

I. Overview

Figure 1:
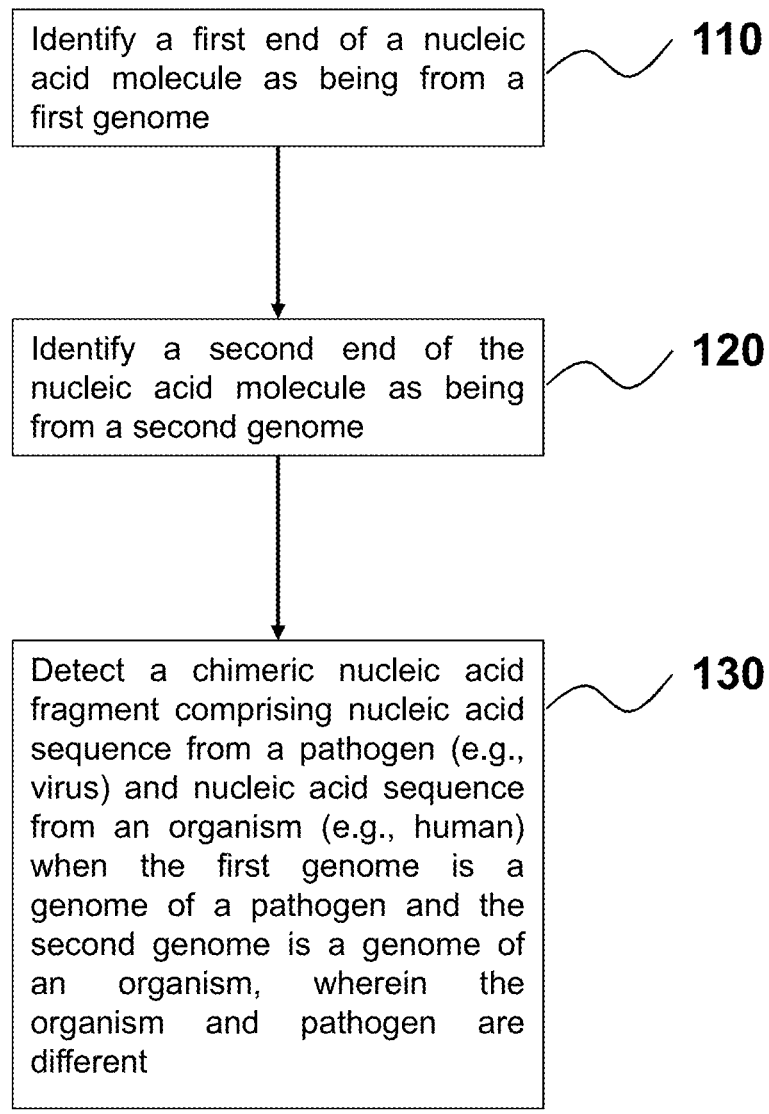
FIG. 1 is a schematic of a workflow for determining a chimeric nucleic acid fragment comprising nucleic acid sequence from a pathogen (e.g., virus) and nucleic acid sequence from a host organism (e.g., human).

Provided herein are methods and systems for analyzing a biological sample of an organism to identify a chimeric nucleic acid fragment comprising nucleic acid sequence from a pathogen and nucleic acid sequence from the organism (organism-pathogen chimeric nucleic acid fragment). The methods and systems can comprise analyzing, e.g., by a computer system, a plurality of nucleic acid molecules, e.g., cell-free nucleic acid (e.g., DNA) molecules from the biological sample, e.g., plasma, to detect the chimeric nucleic acid fragment comprising nucleic acid sequence from a pathogen and nucleic acid sequence from the organism. Analyzing each of the plurality of nucleic acid molecules, e.g., cell-free nucleic acid (e.g., DNA) molecules can comprise identifying a first end of the respective nucleic acid molecule, e.g., cell-free nucleic acid molecule, as being from a first genome and identifying a second end of the respective nucleic acid molecule, e.g., cell-free nucleic acid molecule, as being from a second genome. A chimeric nucleic acid fragment comprising nucleic acid sequence from a pathogen and nucleic acid sequence from an organism (e.g., host organism) can be detected when the first genome is a genome of a pathogen (e.g., virus, e.g., human papilloma virus (HPV)) and the second genome is a genome of the organism (e.g., human). The methods and systems can further comprise determining a classification of pathology (e.g., cancer) based at least in part on the chimeric nucleic acid fragment comprising nucleic acid sequence from a pathogen (e.g., virus) and nucleic acid sequence from an organism, e.g., host organism, e.g., human. The classification of cancer can be a type of cancer, e.g., cervical cancer or head and neck squamous cell carcinoma.

Also provided herein are methods and systems for analyzing nucleic acid molecules, e.g., cell-free nucleic acid molecules, from a biological sample, e.g., plasma, e.g., by a computer system, to determine a pathogen integration profile. The pathogen integration profile can comprise a position of a breakpoint in a genome of a pathogen (e.g., virus) that integrates in a genome of the organism, e.g., host organism, e.g., human. The methods and systems can further comprise determining a type of pathology based on the pathogen integration profile. The type of pathology can be, e.g., a type of cancer, e.g., cervical cancer or head and neck squamous cell carcinoma (HNSCC), or a state of the subject associated with an increased risk of cancer, e.g., cervical in situ neoplasia or cervical intraepithelial neoplasia.

Also provided herein are methods and systems for detection of a chromosomal rearrangement. In some cases, the methods comprise analyzing nucleic acid molecules, e.g., cell-free nucleic acid molecules, from a biological sample, e.g., plasma, to identify a chimeric nucleic acid fragment comprising a chromosomal rearrangement. The methods and systems can comprise analyzing, e.g., by a computer system, a plurality of nucleic acid molecules, e.g., cell-free nucleic acid (e.g., DNA) molecules from the biological sample, e.g., plasma, to detect the chimeric nucleic acid fragment comprising a chromosomal rearrangement. Analyzing each of the plurality of nucleic acid molecules, e.g., cell-free nucleic acid (e.g., DNA) molecules can comprise identifying a first end of the respective nucleic acid molecule, e.g., cell-free nucleic acid molecule, as being from a first genomic region of the reference genome of the organism and identifying a second end of the respective nucleic acid molecule, e.g., cell-free nucleic acid molecule, as being from a second genomic region of the reference genome of the organism. A chimeric nucleic acid fragment comprising a chromosomal rearrangement can be detected when the relative positioning of the first and second genomic regions in the reference genome of the organism is inconsistent with the relative positioning of the first and second ends in the respective cell-free nucleic acid molecule. In some cases, the methods and systems as described herein comprise analyzing the chimeric nucleic acid fragment comprising a chromosomal rearrangement to detect the chromosomal rearrangement. In some cases, the methods and systems comprise determining a classification of pathology based at least in part on the chromosomal rearrangement.

The methods provided herein can include steps for increasing a likelihood of capturing nucleic acid fragments from cell-free samples that comprise pathogen, e.g., viral, sequence. For example, the methods provided herein can make use of hybridization probes that cover a whole pathogen (e.g., virus) genome, or at least 99%, at least 95%, at least 90%, or at least of 85% of a whole pathogen (e.g., virus) genome, of viruses such as human papilloma virus, e.g., HPV16, HPV18, HPV33; Epstein Barr Virus (EBV); or hepatitis B virus (HBV); for target capture. Use of such hybridization probes for target capture can enrich viral nucleic acid and increase the chance of obtaining chimeric nucleic acid fragments containing both host (e.g., human) and viral nucleic acid for viral integration analysis.

The methods provided herein can provide enhanced sensitivity. For example, the methods and systems provided herein can lack steps for filtering out genomic regions (e.g., human genomic regions) such as repeat regions, e.g., short tandem repeats, short interspersed nuclear element (SINE/Alu), or long terminal repeat/endogenous retroviruses (LTR/ERV1). Eliminating such filters can increase the sensitivity of the methods provided herein.

The methods provided herein can provide enhanced specificity. For example, paired-end reads spanning host, e.g., human, and pathogen, e.g., virus, genome can be used to build local reference sequences that can contain the breakpoint of the pathogen (e.g., virus) integration. Local realignment for those partially mapped paired-end reads can be used to determine the breakpoint in the local reference sequences. Paired-end reads with compatible mapping orientations or strand information can be used for further downstream analysis of viral integration. Reads incompatible with alignment (because of, e.g., incompatible mapping orientations or strand information) can be removed to reduce the artifacts caused by mapping errors or other errors. Such analysis can also rule out those chimeric fragments derived from cross-ligation of different molecules during nucleic acid, e.g., DNA, library preparation (see e.g., FIG. 4). The methods provided herein can test the compatibility of alignments of an organism-pathogen chimeric read (i.e., a sequence read with a breakpoint between a pathogen (e.g., virus) nucleic acid sequence and host (e.g., human) nucleic acid) with reference to the alignment of the majority of reads within the regions of interest. For example, if a pathogen (e.g., virus) integration breakpoint in a chimeric read is not compatible with the strand information present in the majority of reads, such a pathogen (e.g., virus) integration breakpoint can be less confidently called.

Figure 5:
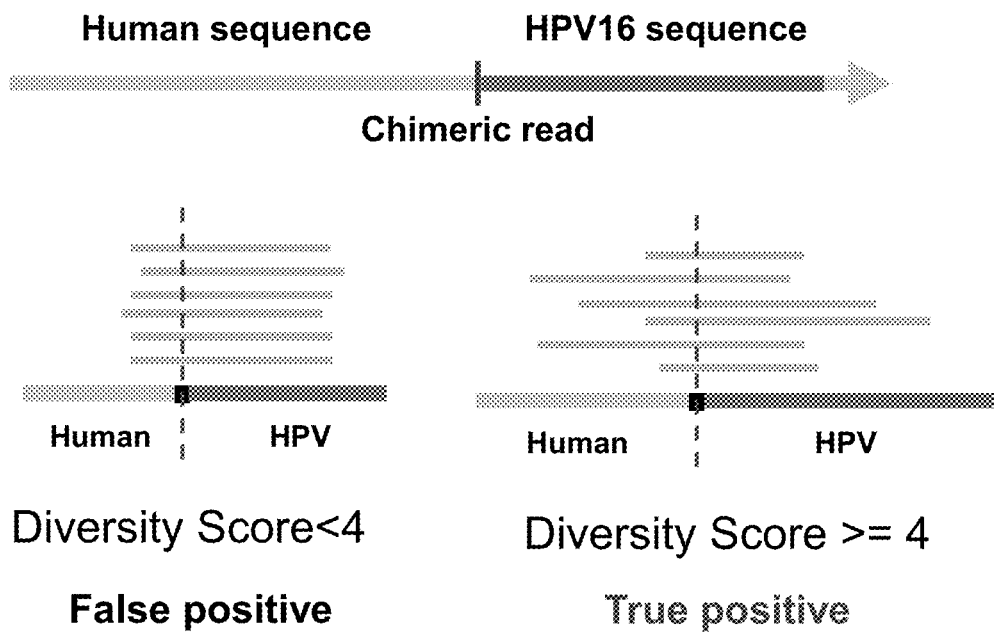
FIG. 5 is a schematic demonstrating candidate integration breakpoints having low (<4) and high (>=4) Diversity Scores.

Methods provided herein can make use of chimeric fragments distributed around integration breakpoints that have sufficient diversity in terms of fragment lengths, fragment end positions and relative locations of breakpoints in chimeric nucleic acid fragments (see e.g., FIG. 5). In some cases, for a particular integration breakpoint, the more diverse the fragment lengths, fragment end positions, and relative locations of breakpoints in chimeric fragments, the higher the confidence of integration.

In some cases, because the viral episomal nucleic acid (e.g., DNA) can be shorter than host (e.g., human) nucleic acid (e.g., DNA), chimeric nucleic acid fragments generated as a result of viral nucleic acid (e.g., DNA) integration into a host (e.g., human) genome can be expected to be longer than viral nucleic acid (e.g., DNA) derived from episomes. Thus, the mean or median length of chimeric nucleic acid fragments including a pathogen (e.g., virus) integration breakpoint can be larger than the other pathogen (e.g., virus) nucleic acid (e.g., DNA) from episomes.

Furthermore, in some cases, the methods provided herein do not include a training step involving mathematical modeling (e.g., Hidden Markov Model) for building an ensemble of profile of phylogenetics of available viral genomes. In some cases, the methods provided herein do not include analysis of pathogen (e.g., virus) nucleic acid from a tissue sample. The methods provided herein can make use of a cell-free biological sample, e.g., plasma. Nucleic acid, e.g., DNA, in plasma can be naturally fragmented, and fragmentation patterns can be varied according to the origin of plasma nucleic acid (e.g., DNA, e.g., liver DNA, viral DNA, and tumor DNA). In some cases, the methods provided herein do not include shearing of the nucleic acids from the cell-free biological sample before short-read sequencing.

II. Workflow

The systems and methods provided herein can be used to analyze cell-free nucleic acid molecules comprising sequence from a genome of an organism, e.g., a host organism, e.g., human, and sequence from a genome of a pathogen (e.g., virus, e.g., HPV). In plasma of a human subject, e.g., a patient having a viral-associated malignancy, some of the cell-free nucleic acid molecules can contain sequence of the viral genome and sequence of the human genome. These cell-free nucleic acid molecules in the plasma can be termed chimeric nucleic acid fragments.

FIG. 1 shows a schematic of an exemplary workflow for determining a chimeric nucleic acid fragment comprising sequence from a pathogen and sequence from an organism from a biological sample of the organism. As depicted, methods provided herein for determining a chimeric nucleic acid fragment can comprise identifying a first end of the respective cell-free nucleic acid molecule as being from a first genome (110). The methods can further comprise identifying a second end of the respective cell-free nucleic acid molecule as being from a second genome (120). The methods can further comprise detecting the chimeric nucleic acid fragment when the first genome is a genome of a pathogen and the second genome is a genome of the organism, wherein the organism and pathogen are different (130). The nucleic acid molecule can be a cell-free nucleic acid molecule. The nucleic acid molecule can be from a biological sample. A first end of the nucleic acid molecule can be a 5' or 3' end of the nucleic acid molecule, while a second end of the nucleic acid molecule can be a 3' or 5' end of the nucleic acid molecule. The organism can be a host organism for the pathogen, e.g., a human. The pathogen can be a virus, e.g., HPV, EBV, and HBV.

Also provided herein are methods and systems for determining a pathogen integration profile, e.g., location of one or more pathogen integration breakpoints in a genome of a host organism or a genome of a pathogen, by analyzing nucleic acid molecules from a biological sample. As depicted in FIG. 2, in paired-end sequencing, host-organism-pathogen (e.g., human-viral) chimeric fragments can be detected and display two different forms of sequence read pairs (pairs of sequence reads obtained from the two ends of the same nucleic acid molecule, e.g., cell-free DNA molecule). The two reads of a read pair from a single nucleic acid fragment in paired-end sequencing data can be called mate reads. One type (Type A) can refer to a cell-free nucleic acid molecule (e.g., cell-free DNA) with one sequence read at a first end that is mappable to a host organism reference genome (e.g., human reference genome) and another read at a second end that is mappable to a pathogen reference genome (e.g., virus reference genome), and vice versa.

In some cases, a sequence read maps to, is mappable to, or aligns to, a reference genome, when the sequence read has at least 80%, at least 85%, at least 90%, at least 95%, at least 98%, at 99%, or 100% sequence identity or complementarity to a particular region of a reference genome, e.g., a human reference genome, over the entire sequence read. In some cases, a sequence read maps to, is mappable to, or aligns to, a reference genome, when the sequence read has at least 80% sequence identity or complementarity to a particular region of a reference genome, e.g., a human reference genome, over the entire sequence read. In some cases, a sequence read maps to, is mappable to, or aligns to, a reference genome, when the sequence read is identical or complementary to a particular region of a reference genome, e.g., a human reference genome, with no more than 20, 15, 10, 9, 8, 7, 6, 5, 4, 3, 2, or 1 mismatches, or with zero mismatches. The maximum mismatch number or percentage, or the minimum similarity number or percentage can vary as a selection criterion depending on purposes and contexts of application of the methods and systems provided herein. In some cases, a sequence read maps to, is mappable to, or aligns to, a reference genome, when the sequence read is identical or complementary to a particular region of a reference genome, e.g., a human reference genome, with no more than 2 mismatches. The other fragment type (Type B) can refer to a cell-free nucleic acid molecule (e.g., cell-free DNA) with part of one sequence read at a first end that is mappable to a host organism (e.g., human) genome and the remaining part of the sequence read mappable to a pathogen (e.g., viral) genome ("chimeric read"), and with another sequence read at a second end that is mappable to either the host organism genome or the pathogen genome. As depicted in FIG. 2, Type B host organism-pathogen (e.g., human-viral) chimeric fragment sequence read pairs can have one sequence read mappable to either a host organism genome (e.g., human genome) or a pathogen genome (e.g., viral genome), and the other sequence read having a portion thereof mappable to the host organism (e.g., human) genome and the remaining thereof mappable to the pathogen (e.g., viral) genome. In Type B sequence read pairs, the exact integration breakpoint can be directly identified from the chimeric read. In one example, for identification of Type A fragments, sequence reads can be aligned to reference genomes, e.g., human reference genome and viral reference genome (e.g., HPV reference genome), using SOAP algorithm with a maximum mismatch number of two as a selection criterion. In one example, for identification of Type B fragments, sequence reads can be aligned to reference genomes, e.g., human reference genome and viral reference genome (e.g., HPV reference genome), using Bowtie2 and local alignment program with a maximum mismatch number of three as a selection criterion.

Figure 3A:
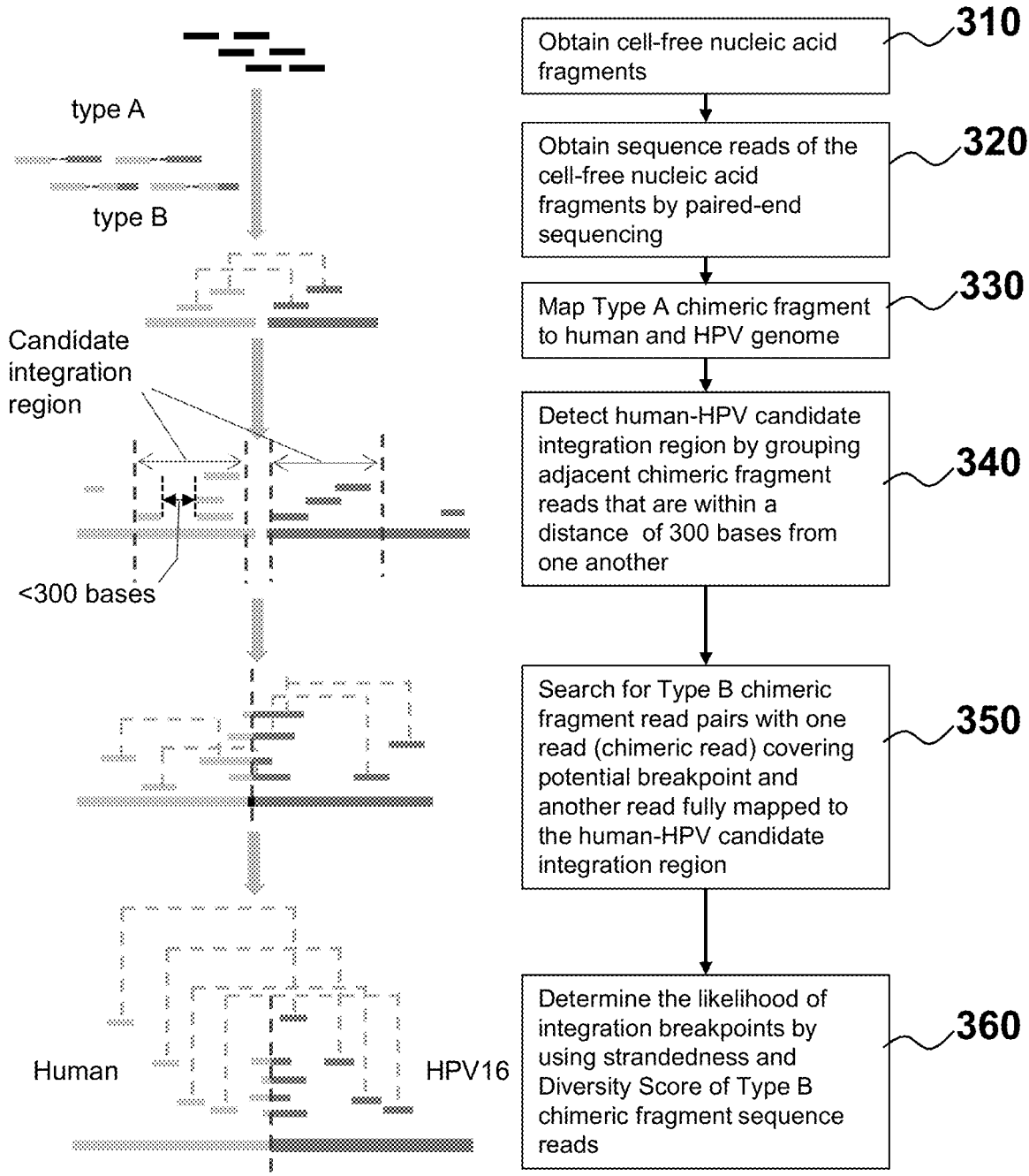
FIG. 3A is a schematic of an exemplary workflow for human papilloma virus (HPV) viral DNA integration analysis.

FIG. 3A shows a schematic of an exemplary workflow for analysis of pathogen (e.g. HPV) viral DNA integration to a host organism (e.g., human) genome using cell-free DNA fragments from plasma (310). Sequence reads of the cell-free DNA fragments from a plasma sample can be obtained by paired-end sequencing of the cell-free DNA fragments (320). After obtaining the sequence read pairs for both ends of the cell-free DNA fragments from a plasma sample, Type A fragments can be identified by aligning one sequence read to a reference genome of human and its mate read to a reference genome of HPV (330). Candidate integration regions in the human and HPV reference genomes can be detected by grouping chimeric fragment sequence reads (340) with adjacent coordinates in the human and HPV reference genomes, respectively. Type B chimeric fragment read pairs with one sequence read covering a potential breakpoint and another sequence read fully mapped to a same candidate region can then be searched for (350). The candidate integration breakpoints can be further filtered by determining the strandedness of Type A and Type B fragment sequence reads and by determining Diversity Score of the chimeric reads of Type B fragments (360) for each candidate integration breakpoint in order to determine the likelihood of the integration breakpoints.

A. Identification of Organism-Pathogen Candidate Integration Region

The methods and systems provided herein can be used to determine organism-pathogen candidate integration region in a genome of a pathogen (e.g., virus, e.g., HPV) and in a genome of a host organism (e.g., human).

Figure 3B:
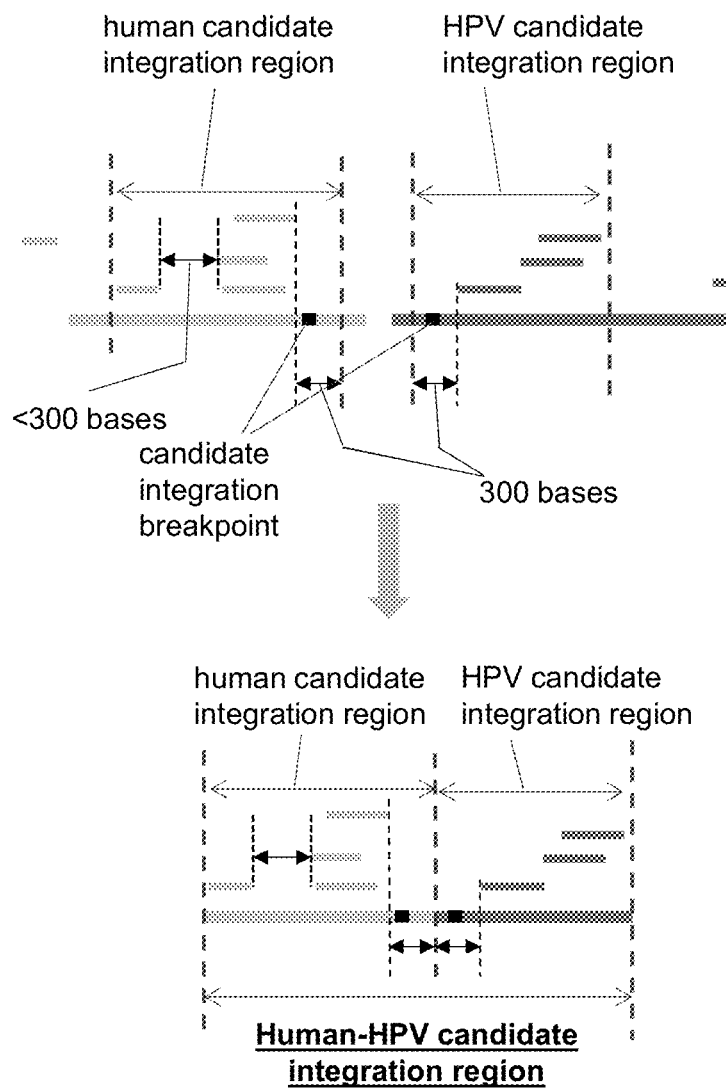
FIG. 3B is a schematic of an exemplary workflow for deducing a human-HPV candidate integration region.

In some examples, Type A organism-pathogen chimeric fragments can be identified by searching for sequence read pairs with one sequence read from a first end of the fragment mapped to a human genome and the other sequence read from a second end of the fragment mapped to the pathogen (e.g., virus, e.g., HPV) genome. The Type A organism-pathogen chimeric fragment sequence reads can be used for determining candidate integration regions in the reference genomes of host organism and pathogen, respectively. In some examples, all Type A chimeric fragment reads can be grouped together when the chimeric fragment reads are overlapping or are adjacent to each other in reference genomes of host and pathogen, respectively, to identify candidate integration regions in the reference genomes of both host and pathogen. In some examples, chimeric fragments with the same start and end outer coordinates can be removed as they can be suspected to be PCR duplicates. In some examples, after the removal of putative PCR duplicates, all remaining Type A chimeric fragment reads can then be pooled together to group nucleotide coordinates that are overlapping or are adjacent to each other in reference genomes of host and pathogen, respectively, to identify candidate integration regions in the reference genomes of both host and pathogen. In the example as depicted in FIG. 3A, each candidate integration region on the human genome would have one or more corresponding integration regions on the HPV genome, and vice versa. Distance between sequence reads can be the distance between the two closest nucleotides on the two adjacent reads on a reference genome. Adjacent "host organism reads" (sequence reads aligning to the reference genome of the host organism) or their corresponding adjacent "pathogen reads" (sequence reads aligning to the reference genome of the pathogen) within a predetermined distance in host organism and pathogen reference genomes, respectively, can then be considered as belonging to one candidate integration region. The cutoff value for the predetermined distance can be 300 bases as demonstrated in FIG. 3A. In one example, in one candidate integration region, the distance between any two nearest host sequence reads or between any two nearest pathogen sequence reads is no more than 300 bases. In one example, host sequence reads whose distances from its nearest reads are more than 300 bases apart are not included in the same candidate integration region. In one example, pathogen sequence reads whose distances from their nearest read are more than 300 bases apart are not included in the same candidate integration region. In some examples, when determining a candidate integration region, after grouping Type A chimeric fragment reads, the boundary of the outermost Type A fragment read(s) on the side of a candidate breakpoint can be further expanded toward the candidate breakpoint, for example, by 100 bases, 200 bases, 300 bases 400 bases, 500 bases, or 600 bases, so that in some cases, the candidate integration region on the host organism reference genome, the pathogen reference genome, or both, can cover the candidate integration breakpoint. The expansion as described above can be by any appropriate number of bases. FIG. 3B illustrates an exemplary process of deducing an organism-pathogen candidate integration region (e.g., human-HPV candidate integration region) by merging the host organism candidate integration region and the pathogen candidate integration region. As shown in the figure, human candidate integration region and HPV candidate integration region can be deduced by grouping Type A chimeric fragment reads according to their coordinates in the reference genomes of human and HPV, respectively. In this example, the cutoff value for the predetermined distance between any adjacent human reads or HPV reads within the same candidate integration region is 300 bases. Furthermore, for both the human and HPV candidate integration regions, the boundaries are expanded toward the side of a candidate integration breakpoint for 300 bases in this example. As shown in the figure, in this case, 300 bases expansion renders both human and HPV candidate integration regions to cover the candidate breakpoint. Subsequently, a human-HPV candidate integration region can be deduced by merging the human and HPV candidate integration regions along the boundaries on the side of the candidate breakpoint. In some examples, the number of Type A chimeric fragment sequence read pairs within an organism-pathogen candidate integration region can also be used to evaluate and determine the candidate integration region.

1. Sequence Read Alignment to a Reference Genome

The alignment of sequence reads of a cell-free nucleic acid molecule from a sample from a subject can be performed by any appropriate bioinformatics algorithms, programs, toolkits, or packages. For instance, one can use the short oligonucleotide analysis package (SOAP) as an alignment tool for applications of methods and systems as provided herein. Examples of short sequence reads analysis tools that can be used in the methods and systems provided herein include Arioc, BarraCUDA, BBMap, BFAST, Big-BWA, BLASTN, BLAT, Bowtie, Bowtie2, BWA, BWA-PSSM, CASHX, Cloudburst, CUDA-EC, CUSHAW, CUSHAW2, CUSHAW2-GPU, CUSHAW3, drFAST, ELAND, ERNE, GASSST, GEM, Genalice MAP, Geneious Assembler, GensearchNGS, GMAP and GSNAP, GNU-MAP, HIVE-hexagon, Isaac, LAST, MAQ, mrFAST, mrs-FAST, MOM, MOSAIK, MPscan, Novoalign & NovoalignCS, NextGENe, NextGenMap, Omixon Variant Toolkit, PALMapper, Partek Flow, PASS, PerM, PRIMEX, QPalma, RazerS, REAL, cREAL, RMAP, rNA, RTG Investigator, Segemehl, SeqMap, Shrec, SHRiMP, SLIDER, SOAP, SOAP2, SOAP3, SOAP3-dp, SOCS, SparkBWA, SSAHA, SSAHA2, Stampy, SToRM, Subread, Subjunc, Taipan, UGENE, VelociMapper, XpressAlign, and ZOOM.

A number of consecutive nucleotides ("a sequence stretch") in a sequence read can be used to align to a reference genome to make a call regarding alignment. For example, the alignment can comprise aligning at least 4, at least 6, at least 8, at least 10, at least 12, at least 14, at least 16, at least 18, at least 20, at least 22, at least 24, at least 25, at least 26, at least 28, at least 30, at least 32, at least 34, at least 35, at least 36, at least 38, at least 40, at least 42, at least 44, at least 45, at least 46, at least 48, at least 50, at least 52, at least 54, at least 55, at least 56, at least 58, at least 60, at least 62, at least 64, at least 65, at least 66, at least 67, at least 68, at least 69, at least 70, at least 71, at least 72, at least 73, at least 74, at least 75, at least 76, at least 78, at least 80, at least 82, at least 84, at least 85, at least 86, at least 88, at least 90, at least 92, at least 94, at least 95, at least 96, at least 98, at least 100, at least 102, at least 104, at least 106, at least 108, at least 110, at least 112, at least 114, at least 116, at least 118, at least 120, at least 122, at least 124, at least 126, at least 128, at least 130, at least 132, at least 134, at least 136, at least 138, at least 140, at least 142, at least 145, at least 146, at least 148, or at least 150 consecutive nucleotides of a sequence read to a reference genome, e.g., a reference genome of a pathogen, or a reference genome of a host organism. In some cases, alignment as mentioned herein can comprise aligning at most 5, at most 7, at most 9, at most 11, at most 13, at most 15, at most 17, at most 19, at most 21, at most 23, at most 25, at most 27, at most 29, at most 31, at most 33, at most 35, at most 37, at most 39, at most 41, at most 43, at most 45, at most 47, at most 49, at most 51, at most 53, at most 55, at most 57, at most 59, at most 61, at most 63, at most 65, at most 67, at most 68, at most 69, at most 70, at most 71, at most 72, at most 73, at most 74, at most 75, at most 76, at most 78, at most 80, at most 81, at most 83, at most 85, at most 87, at most 89, at most 91, at most 93, at most 95, at most 97, at most 99, at most 101, at most 103, at most 105, at most 107, at most 109, at most 111, at most 113, at most 115, at most 117, at most 119, at most 121, at most 123, at most 125, at most 127, at most 129, at most 131, at most 133, at most 135, at most 137, at most 139, at most 141, at most 143, at most 145, at most 147, at most 149, or at most 151 consecutive nucleotides of a sequence read to a reference genome, e.g., a reference genome of a pathogen, or a reference genome of a host organism. In some instances, alignment as mentioned herein comprises aligning about 20, about 22, about 24, about 25, about 26, about 28, about 30, about 32, about 34, about 35, about 36, about 38, about 40, about 42, about 44, about 45, about 46, about 48, about 50, about 52, about 54, about 55, about 56, about 58, about 60, about 62, about 64, about 65, about 66, about 67, about 68, about 69, about 70, about 71, about 72, about 73, about 74, about 75, about 76, about 78, about 80, about 82, about 84, about 85, about 86, about 88, about 90, about 92, about 94, about 95, about 96, about 98, about 100, about 102, about 104, about 106, about 108, about 110, about 112, about 114, about 116, about 118, about 120, about 122, about 124, about 126, about 128, about 130, about 132, about 134, about 136, about 138, about 140, about 142, about 145, about 146, about 148, about 150, about 152, about 154, about 155, about 156, about 158, about 160, about 162, about 164, about 165, about 166, about 168, about 170, about 172, about 174, about 175, about 176, about 178, about 180, about 185, about 190, about 195, or about 200 consecutive nucleotides of a sequence read to a reference genome, e.g., a reference genome of a pathogen, or a reference genome of a host organism.

In some cases, an alignment call is made when the sequence stretch has at least 80%, at least 85%, at least 90%, at least 95%, at least 98%, at 99%, or 100% sequence identity or complementarity to a particular region of a reference genome, e.g., a human reference genome, over the entire sequence read. In some cases, an alignment call is made when the sequence stretch has at least 80% sequence identity or complementarity to a particular region of a reference genome, e.g., a human reference genome, over the entire sequence read. In some cases, an alignment call is made when the sequence stretch is identical or complementary to a particular region of a reference genome, e.g., a human reference genome, with no more than 20, 15, 10, 9, 8, 7, 6, 5, 4, 3, 2, or 1 mismatches, or with zero mismatches. In some cases, an alignment call is made when the sequence stretch is identical or complementary to a particular region of a reference genome, e.g., a human reference genome, with no more than 2 mismatches. The maximum mismatch number or percentage, or the minimum similarity number or percentage can vary as a selection criterion depending on purposes and contexts of application of the methods and systems provided herein.

2. Types of Reference Genomes

Sequence reads generated using methods and systems provided herein can be aligned to one or more reference genomes, such as a reference genome of a pathogen and a reference genome of a host organism. A reference genome of a pathogen in some cases can be a viral genome, for instance, a HPV viral genome. The reference genome can be a consensus genome, or a reference genome of a specific strain of a virus. In some cases, a pathogen genome comprises RNA, the alignment to a reference genome of a pathogen can comprise converting the sequence information of the sequence reads into a RNA sequence, or converting the RNA genome sequence into sequence of its complementary DNA. A host organism can be a human or a non-human animal. Examples of human reference genomes include GRChg37, GRChg37, NCBI Build 34, NCBI Build 35, and NCBI Build 36.1. The human reference genome can be the genome of an individual human. The human genome can be a consensus sequence.

3. Cutoff Values for Integration Region

Examples of the cutoff value for the predetermined distance between host organism read and host organism read, or between pathogen read and pathogen read, in defining the candidate integration region include about 10, about 15, about 20, about 25, about 30, about 35, about 40, about 45, about 50, about 55, about 60, about 65, about 70, about 75, about 80, about 85, about 90, about 95, about 100, about 105, about 110, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 460, about 470, about 480, about 490, or about 500 bases. A cutoff value for the predetermined distance between host organism read and host organism read, or between pathogen read and pathogen read, in defining the candidate integration region can be at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, at least 430, at least 435, at least 440, at least 445, at least 450, at least 460, at least 470, at least 480, at least 490, or at least 500 bases. In some instance, the predetermined distance between host organism read and host organism read, or between pathogen read and pathogen read, in defining the candidate integration region can be at most 10, at most 15, at most 20, at most 25, at most 30, at most 35, at most 40, at most 45, at most 50, at most 55, at most 60, at most 65, at most 70, at most 75, at most 80, at most 85, at most 90, at most 95, at most 100, at most 105, at most 110, at most 120, at most 125, at most 130, at most 135, at most 140, at most 145, at most 150, at most 155, at most 160, at most 165, at most 170, at most 175, at most 180, at most 185, at most 190, at most 195, at most 200, at most 205, at most 210, at most 215, at most 220, at most 225, at most 230, at most 235, at most 240, at most 245, at most 250, at most 255, at most 260, at most 265, at most 270, at most 275, at most 280, at most 285, at most 290, at most 295, at most 300, at most 305, at most 310, at most 315, at most 320, at most 325, at most 330, at most 335, at most 340, at most 345, at most 350, at most 355, at most 360, at most 365, at most 370, at most 375, at most 380, at most 385, at most 390, at most 395, at most 400, at most 405, at most 410, at most 415, at most 420, at most 425, at most 430, at most 435, at most 440, at most 445, at most 450, at most 460, at most 470, at most 480, at most 490, or at most 500 bases.

The number of chimeric fragment sequence read pairs within an organism-pathogen candidate integration region can be used to evaluate and screen for candidate integration region. For example, each organism-pathogen candidate integration region can have at least two organism-pathogen (e.g., human-HPV) chimeric fragment sequence read pairs which are not PCR duplicates, e.g., reads with the same start and end outer coordinates. In some instances, each organism-pathogen candidate integration region can have at least 3, 4, 5, 6, 7, 8, 9, 10, 11, 12, 15, 20, 50, 100, 200, 1000, 10,000, 50,000, 100,000, or more organism-pathogen (e.g., human-HPV) chimeric fragment sequence read pairs which are not PCR duplicates, e.g., reads with the same start and end outer coordinates.

B. Strand Orientation and Deduced Integration Breakpoint

The number of chimeric fragment sequence read pairs within an organism-pathogen candidate integration region can be used to evaluate and screen for candidate integration regions. For example, each organism-pathogen candidate integration region can have at least two organism-pathogen (e.g., human-HPV) chimeric fragment sequence read pairs which are not PCR duplicates, e.g., reads with the same start and end outer coordinates. In some instances, each organism-pathogen candidate integration region can have at least 3, 4, 5, 6, 7, 8, 9, 10, 11, 12, 15, 20, 50, 100, 200, 1000, 10,000, 50,000, 100,000, or more organism-pathogen (e.g., human-HPV) chimeric fragment sequence read pairs which are not PCR duplicates, e.g., reads with the same start and end outer coordinates.

Strandedness of the sequence reads generated by paired-end sequencing can be used to determine the likelihood of integration breakpoints. After identification of potential candidate integration regions, strand orientations of a host organism sequence read and a pathogen sequence read in the organism-pathogen chimeric fragment sequence read pairs can be used to eliminate organism-pathogen chimeric fragments generated in vitro (e.g., by in vitro ligation). The integration regions in the host organism and pathogen genomes can be deduced based on the strand orientations of the host organism sequence read and the pathogen sequence read, either upstream or downstream of the host organism and pathogen sequence reads. Type B chimeric fragment sequence read pairs with chimeric reads having inconsistent orientations compared with Type A chimeric fragment sequence read pairs that are used for deducing candidate integration regions can be filtered out. When Type A chimeric fragment sequence read pairs are grouped for determination of candidate integration regions, there can be Type A sequence read pairs having different strand orientations (or strandedness patterns) that are grouped together. In some cases, there can be up to four possible different strand orientations in a given sample: "+/+," "−/−," "+/−," "−/+." where + stands for forward strand when the sequence read matches a sequence in a reference genome, and − stands for reverse strand when the sequence read is complement to a sequence in a reference genome; and the sequence read aligning to host organism genome precedes the sequence read aligning to pathogen genome in expression terms like "+/+," "−/−," "+/−," and "−/+." In some cases, numbers of Type A chimeric fragment sequence read pairs that have each of the four possible different strand orientations are counted. In some cases, Type A chimeric fragment sequence read pairs, which have the majority strand orientation in a group are used for deducing candidate integration regions. In some cases, the number of Type A chimeric fragment sequence read pairs having the majority strand orientation does not exceed 50% of total Type A chimeric fragment sequence read pairs in the group. In some cases, the number of Type A chimeric fragment sequence read pairs having the majority strand orientation exceeds any other strand orientations. FIG. 4 shows exemplary analyses of strand orientation of the sequence read pairs of the cell-free DNA fragments. In this example, human-HPV chimeric sequence read pairs are analyzed. As shown in the schematic of FIG. 4, when the majority of Type A fragment sequence read pairs (3 out of 4) have + strand of human sequence read and − strand of HPV sequence read, the remaining Type A fragment sequence read pair, which has + strand of human sequence read and + strand of HPV sequence read, can be determined as filtered out as "false" read pair. Type B chimeric fragment sequence read pairs can thus be screened based on their strand orientations. In this example, the Type B sequence read pair with chimeric read having inconsistent strand orientation with the strandedness of majority of the Type A fragment sequence read pairs can be filtered out as a "false" read. The table in FIG. 4 lists four different situations of the strand orientation of the majority of Type A human-HPV fragment sequence read pairs in candidate integration regions, and the corresponding expected strand orientation of human-HPV chimeric reads in the same candidate integration region.

C. Identification of Integration Breakpoints

Type B chimeric fragment read pairs or chimeric reads in Type B chimeric fragment read pairs as exemplified in FIG. 2 can be detected by using short sequence reads analysis tools complemented with local alignment functions. For instance, Bowtie2 software can be used for the analysis, and local alignment function can be useful for aligning short nucleotide stretches ("bins") to a host organism reference genome or a pathogen reference genome. The short nucleotide stretches can contain at least 4, at least 5, at least 6, at least 7, at least 8, at least 9, at least 10, at least 12, or at least 15 bases. In some instances, the short nucleotide stretches can contain at most 50, at most 30, at most 25, at most 24, at most 23, at most 22, at most 21, at most 20, at most 19, at most 18, at most 17, at most 16, at most 14, at most 13, at most 11, at most 9, at most 8, at most 7, at most 6, at most 5, or at most 4 bases. The short nucleotide stretches can contain about 4, about 5, about 6, about 7, about 8, about 9, about 10, about 11, about 12, about 15, about 18, about 20, about 22, about 24, about 25, about 30, or about 50 bases. In some instances, the minimum mapping stretches can be 4 bp. In some cases, the alignment can be performed stepwise. For example, alignment can start with a relatively longer stretch length, e.g., about 30 bases or about 22 bases, to locally map the reads to the reference genome of either human or HPV, in order to identify chimeric reads, each of which has one part aligning to human reference genome and the remaining part aligning to HPV reference genome. Once the chimeric reads are identified, the shorter "part" of a chimeric read, e.g., the part of the chimeric read that is mappable to either human genome or HPV genome and is shorter than the other part of the chimeric read, can then be subject to further alignment using a relatively shorter stretch length, e.g., about 4 bases, to the reference genome of either human or HPV, in order to achieve finer alignment to either reference genome, thereby deducing a candidate integration breakpoint. The short nucleotide stretch length can be adjusted depending on various parameters, including, but not limited to, species of pathogen and host organism, variables of various steps of the sequencing assay like amplification, adaptor ligation, sequencing-by-synthesis, sequencing depth, and length of sequence reads, as well as expected sensitivity and specificity for the determination of pathogen integration breakpoints. In some cases, the alignment can be performed in one step using an appropriate local sequence alignment algorithm. For instance, a chimeric read can be detected by the alignment of part of its sequence to a host organism genome or another part to a pathogen genome using Smith-Waterman based dynamic algorithm.

Human-HPV chimeric reads can be identified within candidate integration regions to determine the potential integration breakpoints. In this example, an integration breakpoint can be defined as the boundary of where the HPV DNA is juxtaposed against human DNA. As discussed above, strand orientation of chimeric reads and Type A chimeric fragment read pairs that are used for constructing the candidate regions can be consistent. With this information, the relative location of a potential breakpoint can be further deduced by combining the strand information of the candidate regions and chimeric reads. The table in FIG. 4 further lays out exemplary situations where and how orientations of chimeric fragments have consistent strand orientation with chimeric fragments with human-HPV chimeric read. Expected relative locations of breakpoint to human or HPV genomic sequence are also given for each exemplary situation.

When identifying and analyzing Type B chimeric reads, if the longer part of potential human-HPV chimeric read (either read in paired-end sequencing) is mappable on the human side of a candidate region, alignment can be tested between the shorter part of the chimeric read and the HPV side of the candidate region. Similarly, if the longer part of the potential human-HPV chimeric read (either read in paired-end sequencing) is mappable on the HPV side of a candidate region, alignment can be tested between the shorter part of the chimeric read and the human side of the candidate region. Because the minimum mapping length of the shorter part of a chimeric read can be short, it is possible by chance the short mapping stretches are mappable to multiple regions on either human or HPV genome. Therefore, when the mapping position of the short sequence anchor is within a short predetermined distance of the potential breakpoint, the mapping position can be considered as a putative hit, and as a consequence, the corresponding reads can be regarded as the chimeric reads covering the integration breakpoint.

D. Screening for Highly Confident Integration Breakpoints

For the breakpoints covered by multiple chimeric reads, a diversity test can be used to evaluate the integration breakpoints identified following the protocols as mentioned above and to filter out potential false positive breakpoints. True breakpoints can be covered by multiple chimeric fragments with different lengths of sequences that align to host organism or pathogen reference genome, which therefore have more diversity. Potential integration breakpoints can be evaluated by examining the diversity of the chimeric reads that cover the integration breakpoints, e.g., the diversity of the lengths of sequences of the chimeric reads that align to host organism or pathogen reference genome. A Diversity Score for examining the diversity of the chimeric reads can be calculated as below:

$$\frac{\sigma 1 + \sigma 2}{\max\left(\frac{\sigma 1}{\sigma 2}, \frac{\sigma 2}{\sigma 1}\right)},$$

where

σ1: the standard deviation of lengths of portion of chimeric read aligning to host organism reference genome;

σ2: the standard deviation of lengths of portion of chimeric read aligning to pathogen reference genome.

The integration breakpoints can then be sorted by the Diversity Score. In some cases, the higher the Diversity Score, the higher the likelihood can be that the identified integration breakpoint is true (see e.g., FIG. 5). In some examples, the cutoff Diversity Score can be set as 4, so that the integration breakpoints with a Diversity Score below 4 are excluded, while the remaining integration breakpoints that have Diversity Score of at least 4 can be regarded as from the actual HPV integration events. In some instances, the cutoff Diversity Score is set as about 0.1, about 0.2, about 0.4, about 0.6, about 0.8, about 1, about 1.2, about 1.4, about 1.6, about 1.8, about 2.0, about 2.2, about 2.4, about 2.5, about 2.6, about 2.8, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.2, about 5.4, about 5.6, about 5.8, about 6.0, about 6.5, about 7.0, about 7.5, about 8, about 8.5, about 9, about 9.5, about 10, about 20, about 30, about 40, about 50, about 60, about 80, or about 100. In some instances, the cutoff Diversity Score can be at most 0.1, at most 0.2, at most 0.4, at most 0.6, at most 0.8, at most 1, at most 1.2, at most 1.4, at most 1.6, at most 1.8, at most 2.0, at most 2.2, at most 2.4, at most 2.5, at most 2.6, at most 2.8, at most 3.0, at most 3.1, at most 3.2, at most 3.3, at most 3.4, at most 3.5, at most 3.6, at most 3.7, at most 3.8, at most 3.9, at most 4.0, at most 4.1, at most 4.2, at most 4.3, at most 4.4, at most 4.5, at most 4.6, at most 4.7, at most 4.8, at most 4.9, at most 5.0, at most 5.2, at most 5.4, at most 5.6, at most 5.8, at most 6.0, at most 6.5, at most 7.0, at most 7.5, at most 8, at most 8.5, at most 9, at most 9.5, or at most 10. In other instances, the cutoff Diversity Score can be at least 1, at least 1.2, at least 1.4, at least 1.6, at least 1.8, at least 2.0, at least 2.2, at least 2.4, at least 2.5, at least 2.6, at least 2.8, at least 3.0, at least 3.1, at least 3.2, at least 3.3, at least 3.4, at least 3.5, at least 3.6, at least 3.7, at least 3.8, at least 3.9, at least 4.0, at least 4.1, at least 4.2, at least 4.3, at least 4.4, at least 4.5, at least 4.6, at least 4.7, at least 4.8, at least 4.9, at least 5.0, at least 5.2, at least 5.4, at least 5.6, at least 5.8, at least 6.0, at least 6.5, at least 7.0, at least 7.5, at least 8, at least 8.5, at least 9, at least 9.5, at least 10, at least 20, at least 30, at least 40, at least 50, at least 60, at least 80, or at least 100.

One or more of the various cutoff values as mentioned herein can be adjusted depending on a number of parameters. These variables can be adjusted in order to achieve desirable assessment results, e.g., sensitivity and specificity in determination of the pathogen integration breakpoints. The various cutoff values that can be adjusted according to the methods provided herein include alignment length for searching and identifying Type A chimeric fragment sequence read pairs, cutoff value for distance between reads in defining the integration region, length of the short nucleotide bins for alignment during searching and identifying Type B chimeric fragment sequence reads, and cutoff Diversity Score. One or more of these variables can be adjusted depending on a number of parameters, including context of the sample analysis, e.g., species of the pathogen and the host organism, type of cancer to be analyzed, age, gender, and health condition of the host organism, variables of the various steps of the sequencing assay like amplification, adaptor ligation, sequencing-by-synthesis, sequencing depth, and length of sequence reads, as well as expected outcome for the sample analysis, for instance, sensitivity and specificity for the determination of pathogen integration breakpoints. In some instances, variable adjustment can be evaluated and/or confirmed by other assays. For example, in patients with a certain type of cancer, e.g., cervical carcinoma, HPV integration breakpoints can be determined by analyzing cell-free DNA in plasma sample according to methods and systems provided herein. Different lists of candidate HPV integration breakpoints can be deduced through adjusting one or more of the variables as discussed herein. These lists of candidate HPV integration breakpoints can then be compared against HPV integration breakpoints determined by analyzing tumor tissue sample from the same patient. In some cases, whole genome sequencing or other next-generation sequencing technologies can be used for such analysis. In some cases, variables can be optimized through comparisons in order to obtain accurate information about the pathogen integration profile in the subject.

E. Pathogen Integration Index

The pathogen integration profile as described herein can comprise a pathogen integration index. Some aspects of the present disclosure also provide methods and systems for determining a pathogen integration index by analyzing nucleic acid molecules from a biological sample. An integration index can be an odds ratio of organism-pathogen chimeric nucleic acid molecules over total number of nucleic acid molecules in a biological sample. In some instances, integration index is determined based on a number of chimeric fragment sequence read pairs as discussed above. For example, the number of chimeric read pairs (e.g., Type A fragment read pairs, Type B fragment read pairs, or both) can be determined during sample analysis, e.g., sequencing analysis. In some examples, the pathogen integration index is calculated by dividing the number of organism-pathogen chimeric read pairs (e.g., human-HPV chimeric read pairs) by the number of pathogen fragment read pairs (e.g., HPV fragment read pairs). HPV fragment read pair can be a pair of paired-end sequence reads, both of which map to a genome of the pathogen (e.g., HPV).

In some examples, the integration index can comprise location information. For instance, an integration index can be computed for each of a location in a genome of a pathogen, a genome of a host organism, or both. In some cases, for a location (e.g., nucleotide coordinate) in a genome of pathogen, the number of organism-pathogen chimeric fragment read pairs ending at said location can be determined, and the number of pathogen fragment read pairs ending at said location can also be determined. An integration index for said location can thus be calculated by dividing the number of organism-pathogen chimeric fragment read pairs ending at said location by the number of pathogen fragment read pairs ending at said location. Other calculation methods can also be used for determining the integration index, as long as it reflects the abundance of organism-pathogen chimeric fragments in the biological sample.

The integration index can be analyzed at a genomewide or a locus-specific level. At a locus-specific level, the index can be calculated with respect to any site along the viral genome of at least 1 bp in size. In one example, integration index can be used to predict the risk or likelihood of cancer development. For instance, in some cases, the higher the integration index is, the more likely the cancer can develop in the subject from whom the sample is obtained. In yet another example, the distribution of pathogen integration indices along the viral genome (locus-specific level of analysis) can be distinct across different tumor types. For example, HPV integration index was shown to be different between patients with cervical cancers and HNSCC (FIG. 7), thus informing the tumor origin. Calculation of integration index can be based on, for example, the ratio of Type A viral-human chimeric fragments to the total viral-only DNA. The above-mentioned filtering steps for identifying the integration breakpoints may or may not be applied in the calculation of integration index. For example, any paired-end reads for which one end aligns to the viral genome and the other aligns to the human genome, e.g., Type A chimeric fragments, can be used for calculation of the integration index without any filtering. In another example, the proportion of the total number of Type A and Type B chimeric fragments can be used for calculating the integration index.

It should be understood that while the detailed exemplary workflow described above focuses on analysis of sequence reads from paired-end sequencing on organism-pathogen chimeric cell-free nucleic acid fragments, especially human-HPV chimeric cell-free DNA fragments, similar concepts and methodologies can be applied to situations where other sequencing technologies are used and where not necessarily merely end sequence information is obtained, for example, when sequencing technologies like ion torrent sequencing and nanopore sequencing are used, in order to determine the integration regions and/or breakpoints; similar concepts and methodologies can also be applied to situations where other combinations of pathogen and host organism and/or other nucleic acid molecules, either acellular or cellular, are of concern.

III. Pathogen Integration Profile

A pathogen integration profile can comprise a location of one or more pathogen integration breakpoints in a pathogen genome, a host organism genome, or both. A pathogen integration profile can comprise a location of one or more integration breakpoints in a pathogen genome or a host organism genome. A pathogen integration profile can be used for determining a classification of pathology, e.g., presence or absence of cancer or precancerous lesions, type of cancer, and stage of cancer.

A pathogen integration profile can comprise one or more "integration breakpoints." An integration breakpoint can be a site in which a pathogen nucleic acid molecule (e.g., viral DNA) integrates into a genome (e.g., human genome) of a host cell that is infected by the pathogen.

Integration of pathogen nucleic acid can result in damage in the integrity of a host organism genome, and in some cases, severe downstream consequences in the host cells. The integration breakpoint in the host organism genome can be an expression sequence that can be translated into a protein. The pathogen integration can cause disruption of the protein production in an infected cell. In some other cases, an integration breakpoint in a host organism genome can be in a transcription regulatory region, e.g., an enhancer or a promoter. Integration of a pathogen nucleic acid sequence can result in dysregulation of gene transcription that is normally regulated by the affected transcription regulatory region. In some instances, the pathogen integration can lead to changes in transcription/translation landscape, cellular functions, or malignant transformation of a normal cell into a cancerous cell. The pathogen nucleic acid molecule can be a pathogen genomic DNA molecule. The pathogen nucleic acid molecule can be a complementary DNA of a pathogen genomic RNA molecule when the pathogen genome comprises RNA molecules, for instance, when the pathogen is a RNA virus, e.g., a retrovirus. In blood of a subject infected by HPV, there can be human-HPV chimeric DNA fragments circulating in the plasma that have both HPV DNA sequence and human DNA sequence. In blood of a subject infected by EBV, there can be human-EBV chimeric DNA fragments circulating in the plasma that have both EBV DNA sequence and human DNA sequence.

Pathogen integration profile can refer to a presence or an absence of a combination of nucleotide sequence from a pathogen genome and nucleotide sequence from a host organism genome in the nucleic acid molecules of concern, a size or length of nucleotide sequence from a pathogen genome in the nucleic acid molecules of concern, a fractional contribution of nucleotide sequence from a pathogen genome in the nucleic acid molecules of concern, sequence pattern of the nucleotide sequence from a pathogen genome in the nucleic acid molecules of concern, a characteristic of a pathogen-host organism junction point in the nucleic acid molecules of concern, location of a breakpoint in a genome of a pathogen that integrates into a genome of the host organism, or location of a breakpoint in a genome of the host organism where the a pathogen nucleic acid molecule is inserted in the host organism genome. In some instances, pathogen integration profile comprises a location of a breakpoint in a genome of a pathogen that integrates in a genome of the host organism.

In some examples, the methods provided herein relate to analyzing a biological sample of an organism to determine a pathogen integration profile. In some cases, the methods can comprise analyzing cell-free nucleic acid molecules from the biological sample to determine a pathogen integration profile. The pathogen integration profile can comprise a position of integration breakpoint in a genome of a pathogen that integrates in a genome of the host organism, a position of integration breakpoint in a genome of the host organism, or both. Breakpoint in general can refer to a position at which a nucleic acid sequence from a first organism is juxtaposed to nucleic acid sequence from a second organism when the nucleic acid sequence from the first organism integrates into the genome of the second organism. In some cases, a breakpoint as discussed herein can be a position where a nucleic acid sequence from a genome of a pathogen is juxtaposed against a nucleic acid sequence from a genome of a host organism. For instance, a breakpoint in a genome of a pathogen can refer to a position in a pathogen genome at which the pathogen genomic DNA breaks and joins a host organism genomic DNA when the pathogen genome is integrated into a host genome. In some instances, the integration process can involve one breakpoint in a pathogen genome. In other instances, the integration process can involve multiple breakpoints in a pathogen genome, e.g., the pathogen genomic DNA breaks up into multiple fragments, e.g., 2, 3, 4, 5, 6, 7, 8, 9, 10, 15, 20, 100, or more, which are inserted into a host organism genome, respectively. In some cases, methods and systems provided herein enables identification of one or more integration breakpoints in nucleic acid molecules from a biological sample. In some cases, methods and systems provided herein enables identification of 2, 3, 4, 5, 6, 7, 8, 9, or even more integration breakpoints in nucleic acid molecules from a biological sample.

IV. Chromosomal Rearrangement

A. Detection of Chromosomal Rearrangement

In some aspects, the present disclosure provides methods of detecting a chromosomal rearrangement. The methods and systems can comprise analyzing, by a computer system, a plurality of nucleic acid molecules, e.g., cell-free nucleic acid (e.g., DNA) molecules from the biological sample, e.g., plasma, to detect the chimeric nucleic acid fragment comprising a chromosomal rearrangement (chromosomal rearrangement chimeric nucleic acid fragment). Analyzing each of the plurality of nucleic acid molecules, e.g., cell-free nucleic acid (e.g., DNA) molecules, can comprise identifying a first end of the respective nucleic acid molecule, e.g., cell-free nucleic acid molecule, as being from a first genomic region of the reference genome of the organism and identifying a second end of the respective nucleic acid molecule, e.g., cell-free nucleic acid molecule, as being from a second genomic region of the reference genome of the organism. A chimeric nucleic acid fragment comprising a chromosomal rearrangement can be detected when the relative positioning of the first and second genomic regions in the reference genome of the organism is inconsistent with the relative positioning of the first and second ends in the respective cell-free nucleic acid molecule.

The relative positioning can refer to a relative distance in a reference genome or a cell-free nucleic acid fragment, or a relative 5' to 3' (or upstream-downstream) relationship. The relative distance can refer to an exact relative distance or a range of relative distance. For instance, the relative positioning can be consistent if the relative distance between the first and second genomic regions in the reference genome and the relative distance between the first and second ends in the cell-free nucleic acid fragment are exactly the same in some cases, or are in the same range (e.g., 100-180 bases or a typical length range of a cell-free nucleic acid fragment) in some other cases. The relative positioning can be inconsistent if the relative distance between the first and second genomic regions in the reference genome and the relative distance between the first and second ends in the cell-free nucleic acid fragment are not exactly the same in some cases, or are not in the same range (e.g., 100-180 bases or a typical length range of a cell-free nucleic acid fragment) in some other cases. The inconsistency can vary depending on the different types of chromosomal rearrangement between the relative positioning of the first and second genomic regions in the reference genome of the organism is inconsistent with the relative positioning of the first and second ends in the respective cell-free nucleic acid molecule. A chromosomal rearrangement can be a translocation, amplification, deletion, inversion, chromosomal arm loss, and chromosomal arm gain.

A translocation can involve inter- or intrachromosomal rearrangement of nucleic acid sequences from two previously separate genomic regions on different chromosome or on the same chromosome, respectively. If a cell-free nucleic acid fragment arises from a genomic region encompassing a translocation event, the two ends of the cell-free nucleic acid fragment can come from two previously separate genomic regions in the organism. In some cases, if the first end of the cell-free nucleic acid fragment aligns to a first genomic region in a reference genome of the organism and the second end of the cell-free nucleic acid fragment aligns to a second genomic region in the reference genome of the organism, the first and second genomic regions in the reference genome can have a distance that is inconsistent with the distance between the first and second ends in the cell-free nucleic acid fragment. For instance, the distance between the first and second genomic regions in the reference genome can be undeterminable, if the first and second genomic regions in the reference genome are on different chromosomes when the two ends of the cell-free nucleic acid fragment span portions of two originally different chromosomes. In some cases, the distance between the first end and second genomic regions in the reference genome can be longer than the distance between the first and second ends in the cell-free nucleic acid fragment if the cell-free nucleic acid fragment spans a location where an intrachromosomal translocation of the chromosome has taken place. In some cases, the relative distance of the first and second genomic regions in the reference genome is compared to an arbitrary cutoff value for determining whether or not the cell-free nucleic acid spans a location where translocation has taken place. For example, the cutoff value can be a distance longer than an expected length of a cell-free nucleic acid fragment. In some cases, the cutoff value can be a distance longer than an expected length of a cell-free nucleic acid fragment minus the lengths of the first and second sequence reads. The cutoff value can be about 100 bases, about 200 bases, about 300 bases, about 400 bases, about 500 bases, about 600 bases, about 800 bases, about 1000 bases, about 1200 bases, about 1500 bases, about 2000 bases, about 300 bases, about 4000 bases, about 5000 bases, about 6000 bases, about 8000 bases, or about $10^4$ bases. The cutoff value can be at least 80 bases, at least 140 bases, at least 180 bases, at least 250 bases, at least 350 bases, at least 450 bases, at least 550 bases, at least 750 bases, at least 900 bases, at least 1100 bases, at least 1250 bases, at least 1800 bases, at least 2500 bases, at least 3500 bases, at least 5500 bases, at least 7500 bases, at least 9000 bases, or at least $10^4$ bases.

An inversion can be a chromosome rearrangement in which a segment of a chromosome is reversed end to end. An inversion can occur when a single chromosome undergoes breakage and rearrangement within itself. If a cell-free nucleic acid fragment arises from a genomic region encompassing an inversion event, the two ends of the cell-free nucleic acid fragment can come from two genomic regions which originally have opposite 5' to 3' relationship. In these cases, if the first end of the cell-free nucleic acid fragment aligns to a first genomic region in a reference genome of the organism and the second end of the cell-free nucleic acid fragment aligns to a second genomic region in the reference genome of the organism, then the first and second genomic regions in the reference genome can have a reverse 5' to 3' relationship as compared to the first and second ends of the cell-free nucleic acid fragment.

An amplification can be a chromosomal rearrangement in which a segment of a chromosome is locally replicated. A cell-free nucleic acid fragment arising from a genomic region encompassing an amplification can have two ends that comprise the same replicated sequence. A deletion can be a chromosomal rearrangement in which a segment of a chromosome is deleted. A cell-free nucleic acid fragment arising from a genomic region encompassing a deletion can have two ends that come from two genomic regions that were previously separated apart by the deleted segment.

The methods can further comprise analyzing the chromosomal rearrangement chimeric nucleic acid fragment to detect the chromosomal rearrangement. Detection of the chromosomal rearrangement can include determining the type of the chromosomal rearrangement, for example, translocation, amplification, deletion, inversion, chromosomal arm loss, or chromosomal arm gain. Detection of the chromosomal rearrangement can also include determining the chromosomal rearrangement breakpoint.

In some cases, the methods comprise identifying Type A chromosomal chimeric sequence read pairs from a plurality of sequence read pairs generated from paired-end sequencing of cell-free nucleic acid molecules from the biological sample. A Type A chromosomal chimeric sequence read pair can have a first sequence read aligning to a first genomic region of a reference genome of the organism and a second sequence read aligning to a second genomic region of the reference genome of the organism; and for each of the Type A chromosomal chimeric sequence read pairs, a relative positioning of the first and second genomic regions in the reference genome of the organism can be inconsistent with a relative positioning of the first and second ends in the respective cell-free nucleic acid molecule. The methods can further comprise grouping the first sequence reads of Type A chromosomal chimeric sequence read pairs that are overlapping or separated within a predetermined distance in the reference genome of the organism, and grouping the second sequence reads of Type A chromosomal chimeric sequence read pairs that are overlapping or separated within a predetermined distance in the reference genome of the organism, thereby determining a candidate rearrangement region comprising candidate regions in the first and second genomic regions of the reference genome of the organism, respectively. A chromosomal rearrangement type (e.g., translocation or inversion) can be deduced based on the Type A chromosomal chimeric sequence read pairs.

The methods can further comprise identifying and analyzing Type B chromosomal chimeric sequence read pairs. Type B chromosomal chimeric sequence read pair can have a first sequence read aligning to the candidate rearrangement region and a second sequence read being a chimeric read, and wherein a portion of the chimeric read aligns to the first genomic region and a remaining portion of the chimeric read aligns to the second genomic region. Based on the Type B chromosomal chimeric sequence read pairs, a chromosomal rearrangement can be determined. For instance, a chromosomal rearrangement breakpoint can be determined by locally aligning the sequence of the chimeric read to the reference genome. Based at least in part on the chromosomal rearrangement breakpoint, a type of the chromosomal rearrangement can be further determined.

In some cases, the methods and systems comprise determining a diversity of chimeric reads of the Type B chromosomal chimeric sequence read pairs, thereby screening the chromosomal rearrangement based on the diversity. The screening can comprise determining a Diversity Score for the Type B chromosomal chimeric sequence read pairs. The Diversity Score can be calculated as:

$$\frac{\sigma 1 + \sigma 2}{\max\left(\frac{\sigma 1}{\sigma 2}, \frac{\sigma 2}{\sigma 1}\right)},$$

wherein σ1 is a standard deviation of lengths of the portion of chimeric read aligning to the first genomic region, and wherein σ2 is a standard deviation of lengths of the remaining portion of chimeric read aligning to the second genomic region.

The methods can include comparing the Diversity Score to a cutoff value. In some cases, if the Diversity Score is equal to or higher than the cutoff value, then the chromosomal rearrangement can be determined based on the chimeric reads. In some cases, the Diversity Score is lower than the cutoff value, the candidate chromosomal rearrangement region can be excluded as a false positive hit. The cutoff value for Diversity Score can be about 0.1, about 0.2, about 0.4, about 0.6, about 0.8, about 1, about 1.2, about 1.4, about 1.6, about 1.8, about 2.0, about 2.2, about 2.4, about 2.5, about 2.6, about 2.8, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.2, about 5.4, about 5.6, about 5.8, about 6.0, about 6.5, about 7.0, about 7.5, about 8, about 8.5, about 9, about 9.5, about 10, about 20, about 30, about 40, about 50, about 60, about 80, or about 100. In some instances, the cutoff Diversity Score can be at most 0.1, at most 0.2, at most 0.4, at most 0.6, at most 0.8, at most 1, at most 1.2, at most 1.4, at most 1.6, at most 1.8, at most 2.0, at most 2.2, at most 2.4, at most 2.5, at most 2.6, at most 2.8, at most 3.0, at most 3.1, at most 3.2, at most 3.3, at most 3.4, at most 3.5, at most 3.6, at most 3.7, at most 3.8, at most 3.9, at most 4.0, at most 4.1, at most 4.2, at most 4.3, at most 4.4, at most 4.5, at most 4.6, at most 4.7, at most 4.8, at most 4.9, at most 5.0, at most 5.2, at most 5.4, at most 5.6, at most 5.8, at most 6.0, at most 6.5, at most 7.0, at most 7.5, at most 8, at most 8.5, at most 9, at most 9.5, or at most 10. In other instances, the cutoff Diversity Score can be at least 1, at least 1.2, at least 1.4, at least 1.6, at least 1.8, at least 2.0, at least 2.2, at least 2.4, at least 2.5, at least 2.6, at least 2.8, at least 3.0, at least 3.1, at least 3.2, at least 3.3, at least 3.4, at least 3.5, at least 3.6, at least 3.7, at least 3.8, at least 3.9, at least 4.0, at least 4.1, at least 4.2, at least 4.3, at least 4.4, at least 4.5, at least 4.6, at least 4.7, at least 4.8, at least 4.9, at least 5.0, at least 5.2, at least 5.4, at least 5.6, at least 5.8, at least 6.0, at least 6.5, at least 7.0, at least 7.5, at least 8, at least 8.5, at least 9, at least 9.5, at least 10, at least 20, at least 30, at least 40, at least 50, at least 60, at least 80, or at least 100.

The methods can include filtering out "false positive" sequence read pairs by strandedness similar as in the methods of detecting pathogen integration breakpoint. The methods can comprise filtering out Type B chromosomal chimeric sequence read pairs that have strandedness pattern inconsistent with the majority strandedness pattern are excluded from the determining the chromosomal rearrangement.

B. Identification of gene fusion in cancer genome

In some aspects, methods and systems as provided herein can be applied to detection of gene fusion in human cancer genome. Gene fusion can include inter- or intrachromosomal rearrangement of nucleic acid sequences from two previously separate genomic regions on different or the same chromosome, respectively. A gene fusion event can result in hybrid genomic fragments ("fusion genes") that share similarities to the hybrid DNA molecules resulted from pathogen integration. Gene fusions can occur from translocation, interstitial deletion, or chromosomal inversion. Gene fusions can play roles in cancer development. Identification of gene fusions can be a diagnostic tool and the fusion genes can be a therapeutic target in anti-cancer treatment. The methods and systems as discussed herein relate to detection of fusion genes from cell-free nucleic acids released from tumor tissue genome. The methods provided herein can render such detection painless and non-invasive, which can aid precision cancer treatment and monitor treatment response with tumor DNA in real time.

C. Identification of Somatic Structural Variation

In some aspects, the methods provided herein can be applied to detection of somatic structural variation in genome. Structural variation can include deletions, duplications, copy-number variants, insertions, inversions and translocations, which can contribute to complex disorders, including autism and cancer. Somatic structural variation can result in the release of chimeric DNA molecules to plasma and can be potentially detected by the integration detection methods as described herein. The methods provided herein can allow precise identification of various kinds of structural variations and can promote the exploration of the pathogenic mechanism and therapeutic method of the diseases related to genome structural variation. Somatic structural variations can be detected noninvasively based on the methods provided herein.

V. Sequencing Methods

Sequencing analysis of a biological sample as described herein can be performed for determining a pathogen integration profile. Methods provided herein can comprise sequencing nucleic acid molecules, e.g., cell-free nucleic acid molecules, cellular nucleic acid molecules, or both, from a biological sample. In some instances, methods provided herein comprise analyzing sequencing results, e.g., sequencing reads, from nucleic acid molecules from a biological sample. Methods and systems provided herein can involve or not involve an active step of sequencing. Methods and systems can comprise or provide means for receiving and processing sequencing data from a sequencer. Methods and systems can also comprise or provide means for providing commands to sequencer to adjust parameter(s) of sequencing process, e.g., commands based on the analysis of the sequencing results.

Commercially available sequencing equipment can be used for methods provided in the present disclosure, such as Illumina sequencing platform and the 454/Roche platform. Sequencing the nucleic acid can be performed using any method known in the art. For example, sequencing can include next generation sequencing. In some instances, sequencing the nucleic acid can be performed using chain termination sequencing, hybridization sequencing, Illumina sequencing (e.g., using reversible terminator dyes), ion torrent semiconductor sequencing, mass spectrophotometry sequencing, massively parallel signature sequencing (MPSS), Maxam-Gilbert sequencing, nanopore sequencing, polony sequencing, pyrosequencing, shotgun sequencing, single molecule real time (SMRT) sequencing, SOLiD sequencing (hybridization using four fluorescently labeled di-base probes), universal sequencing, or any combination thereof.

One sequencing method that can be used in the methods as provided herein can involve paired end sequencing, e.g., using an Illumina "Paired End Module" with its Genome Analyzer. Using this module, after the Genome Analyzer has completed the first sequencing read, the Paired-End Module can direct the resynthesis of the original templates and the second round of cluster generation. By using paired end reads in the methods provided herein, one can obtain sequence information from both ends of the nucleic acid molecules and map both ends to a reference genome, e.g., a genome of a pathogen or a genome of a host organism. After mapping both ends, one can determine a pathogen integration profile according to some embodiments of the methods as provided herein.

During paired-end sequencing, the sequence reads from a first end of the nucleic acid molecule can comprise at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 105, at least 120, at least 125, at least 130, at least 135, at least 140, at least 145, at least 150, at least 155, at least 160, at least 165, at least 170, at least 175, or at least 180 consecutive nucleotides. The sequence reads from a first end of the nucleic acid molecule can comprise at most 24, at most 28, at most 32, at most 38, at most 42, at most 48, at most 52, at most 58, at most 62, at most 68, at most 72, at most 78, at most 82, at most 88, at most 92, at most 98, at most 102, at most 108, at most 122, at most 128, at most 132, at most 138, at most 142, at most 148, at most 152, at most 158, at most 162, at most 168, at most 172, or at most 180 consecutive nucleotides. The sequence reads from a first end of the nucleic acid molecule can comprise about 20, about 25, about 30, about 35, about 40, about 45, about 50, about 55, about 60, about 65, about 70, about 75, about 80, about 85, about 90, about 95, about 100, about 105, about 110, about 105, about 120, about 125, about 130, about 135, about 140, about 145, about 150, about 155, about 160, about 165, about 170, about 175, or about 180 consecutive nucleotides. The sequence reads from a second end of the nucleic acid molecule can comprise at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 105, at least 120, at least 125, at least 130, at least 135, at least 140, at least 145, at least 150, at least 155, at least 160, at least 165, at least 170, at least 175, or at least 180 consecutive nucleotides. The sequence reads from a second end of the nucleic acid molecule can comprise at most 24, at most 28, at most 32, at most 38, at most 42, at most 48, at most 52, at most 58, at most 62, at most 68, at most 72, at most 78, at most 82, at most 88, at most 92, at most 98, at most 102, at most 108, at most 122, at most 128, at most 132, at most 138, at most 142, at most 148, at most 152, at most 158, at most 162, at most 168, at most 172, or at most 180 consecutive nucleotides. The sequence reads from a second end of the nucleic acid molecule can comprise about 20, about 25, about 30, about 35, about 40, about 45, about 50, about 55, about 60, about 65, about 70, about 75, about 80, about 85, about 90, about 95, about 100, about 105, about 110, about 105, about 120, about 125, about 130, about 135, about 140, about 145, about 150, about 155, about 160, about 165, about 170, about 175, or about 180 consecutive nucleotides. In some cases, the sequence reads from a first end of the nucleic acid molecule can comprise at least 75 consecutive nucleotides. In some cases, the sequence reads from a second end of the nucleic acid molecule can comprise at least 75 consecutive nucleotides. The sequence reads from a first end and a second end of a nucleic acid molecule can be of the same length or different lengths. The sequence reads from a plurality of nucleic acid molecules from a biological sample can be of the same length or different lengths.

Sequencing in the methods provided herein can be performed at various sequencing depth. Sequencing depth can refer to the number of times a locus is covered by a sequence read aligned to the locus. The locus can be as small as a nucleotide, or as large as a chromosome arm, or as large as the entire genome. Sequencing depth in the methods provided herein can be 1×, 2×, 5×, 10×, 20×, 25×, 30×, 40×, 50×, 75×, or 100×, etc., where the number before "x" refers to the number of times a locus is covered with a sequence read. Sequencing depth can also be applied to multiple loci, or the whole genome, in which case x can refer to the mean number of times the loci or the haploid genome, or the whole genome, respectively, is sequenced. In some cases, ultra-deep sequencing is performed in the methods described herein, which can refer to performing at least 100× sequencing depth.

The number or the average number of times that a particular nucleotide within the nucleic acid is read during the sequencing process (e.g., the sequencing depth) can be multiple times larger than the length of the nucleic acid being sequenced. In some instances, when the sequencing depth is sufficiently larger (e.g., by at least a factor of 5) than the length of the nucleic acid, the sequencing can be referred to as 'deep sequencing'. In some examples, the sequencing depth can be on average at least about 5 times greater, at least about 10 times greater, at least about 20 times greater, at least about 30 times greater, at least about 40 times greater, at least about 50 times greater, at least about 60 times greater, at least about 70 times greater, at least about 80 times greater, at least about 90 times greater, at least about 100 times greater than the length of the nucleic acid being sequenced. In some cases, the sample can be enriched for a particular analyte (e.g., a nucleic acid fragment, or a cancer-specific nucleic acid fragment).

A sequence read (or sequencing reads) generated in methods provided herein can refer to a string of nucleotides sequenced from any part or all of a nucleic acid molecule. For example, a sequence read can be a short string of nucleotides (e.g., 20-150) complementary to a nucleic acid fragment, a string of nucleotides complementary to an end of a nucleic acid fragment, or a string of nucleotides complementary to an entire nucleic acid fragment that exists in the biological sample. A sequence read can be obtained in a variety of ways, e.g., using sequencing techniques

VI. Other Assays

In some instances, systems and methods of the present disclosure relate to using sequencing technology followed by bioinformatic analyses of the sequence reads to analyze a pathogen integration profile in a biological sample, e.g., to analyze integration breakpoint. Cell-free nucleic acids from a biological sample can be collected and subject to sequencing, e.g., paired-end sequencing. Sequence reads of the cell-free nucleic acids can be analyzed by the methods and systems provided herein in order to determine a position of integration breakpoint in a genome of a pathogen, a genome of a host organism, or both. Other technologies can also be used as an alternative or additive approach for the analysis of integration profile, including, but not limited to, amplification assay and microarray assay.

In some examples, methods provided herein can also comprise analyzing amplification reactions of the nucleic acid molecules from the biological sample. The amplification reactions can comprise a first primer complementary to a first target sequence in the genome of the pathogen, and a second primer complementary to a second target sequence in the genome of the organism. Amplification reactions can be designed to amplify pathogen integration regions where nucleic acid sequence from a pathogen joins nucleic acid sequence from a host organism. Having the knowledge of integration breakpoints characteristic of certain classification of cancer can help design such amplification reactions. In some cases, the amplification reactions comprise polymerase chain reaction (PCR). PCR reactions can start with at least a pair of primers, each one of which is complementary to a sequence flanking the integration breakpoint from a pathogen genome or a host organism genome, respectively. Alternatively, PCR reactions can start with random probes that bind to template sequences randomly. In some cases, amplification reactions can provide cost-effective and fast results regarding the integration breakpoints. PCR reactions can be quantitative, which can provide quantitative insights as to the fractional contribution of different types of pathogen integration events. In some cases, analysis of sequences of amplicons generated by the amplification reactions can also be performed in order to confirm the integration breakpoints. Alternatively or additionally, amplification reactions and sequence analysis of amplicons can be performed as a step of target-specific enrichment, therefore providing potentially more robust readout. Different variants of PCR reactions that can be used for the systems and methods described herein include multiplex-PCR, asymmetric PCR, Klenow-based PCR, nested PCR, quantitative PCR, real time-PCR, hot-start PCR, touchdown PCR, assembly PCR, COLD-PCR (co-amplification at lower denaturation temperature-PCR), two-tailed PCR, ligation-mediated PCR, and methylation-specific PCR. While examples and embodiments have been provided herein, additional techniques and embodiments related to, e.g., digital PCR and random sequencing, can be found in U.S. Pat. No. 8,722,334, filed Oct. 28, 2010, U.S. Provisional Application 60/951,438, filed Jul. 23, 2007, and U.S. Pat. No. 9,121,069, filed Jul. 8, 2013, each of which is entirely incorporated herein by reference.

In some other cases, any other sequence assays, such as microarray assay, can be used to obtain sequence information of nucleic acid molecules, e.g., cell-free nucleic acids, from a biological sample. For instance, the microarray can comprise probes targeting both host genomic sequence and pathogen genomic sequence, in order to detect chimeric fragments as described herein. In other examples, a microarray can be designed to detect a location of pathogen integration breakpoints in nucleic acid molecules that are applied to the microarray.

In some instances, the sample analyses as described herein can be supplemented and/or confirmed by assays with different principles and/or approaches. For example, analyses of cell-free DNA in plasma sample can generate a series of results showing preferred pathogen integration breakpoints that are associated with a particular type of cancer. In some instances, the sensitivity and specificity of these results from cell-free DNA sample can be assessed by sequencing, e.g., whole-genome sequencing, of transformed cancer cells of the particular type, such as from biopsy tumor samples. Alternatively, relatively simpler and cost-effective approaches can also be applied, for instance, qualitative or quantitative PCR reactions can be designed to assess the breakpoints by using sequence information achieved during identification of the candidate breakpoints.

In some instances, systems and methods provided herein relate to a first assay and a second assay for determining a classification of pathology. The first assay can comprise a sequencing assay, e.g., sequencing of nucleic acid molecules from a biological sample followed by bioinformatics analysis of the sequence reads as described herein. The second assay can comprise an amplification assay, microarray assay, or other types of assay. In some examples, the second assay comprises a sequencing assay, whereas the first assay comprises an amplification assay, microarray assay, or other types of assay. In some cases, the first assay, e.g., sequencing assay, is used to determine a pathogen integration profile, e.g., a location of one or more pathogen integration breakpoints in a genome of a pathogen or a genome of a host organism. The pathogen integration profile from the first assay can provide guidance for the second assay, for example, the location of one or more pathogen integration breakpoints can provide guidance for design of PCR probes or microarray probes for the second assay. In some examples, a human subject, e.g., a patient, suspected of being infected by a pathogen, e.g., HPV, can be tested by a first assay for determining a pathogen integration profile. The pathogen integration profile can be used to determine a classification of pathology. The patient can be diagnosed of a disease, e.g., a cancer, e.g., a cervical carcinoma, based at least in part on the first assay. The patient can thus be subject to a second assay, which can be used to continue monitoring the pathogen integration profile in the biological sample from the patient, e.g., after administering a therapy to the patient, or after a surgery is performed on the subject. The continued monitoring of the pathogen integration profile can be used for monitoring of the disease the patient has been diagnosed of, for example, for monitoring the progression or regression of the disease. In some examples, a first assay can be used as a screening assay for one or more diseases/conditions, whereas a second assay can be sued as a confirmation assay for the one or more diseases/conditions.

VII. Classification of Pathology

Analysis of integration breakpoint in a genome of a pathogen that integrates in a genome of an organism can be used to determine a classification of a pathology. For instance, methods provided herein can comprise analysis of viral DNA integration profile, e.g., analysis of a breakpoint in HPV viral genome that integrates in a human host organism genome, and can further comprise determining cancer type based on the viral DNA integration profile. Pathology can generally refer to a human condition or disease that deviates from a healthy condition. Non-limiting examples of pathology that is associated with pathogen integration and the methods and systems provided herein are applicable to can include adult T-cell leukemia, tropical spastic paraparesis, cervical cancer, head and neck cancer, anogenital cancer, Kaposi's sarcoma, Burkitt's lymphoma, hepatocellular carcinoma, Merkel cell carcinoma, AIDS, brain cancer, bone cancer, mesothelioma, prostate cancer, and B-cell lymphoma.

Cancer or tumor can refer to an abnormal mass of tissue wherein the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, a benign tumor does not have the capacity to infiltrate, invade or metastasize to distant sites. A "malignant" tumor can be poorly differentiated (anaplasia), and have characteristically rapid growth accompanied by progressive infiltration, invasion, and destruction of the surrounding tissue. Furthermore, a malignant tumor can have the capacity to metastasize to distant sites.

In some aspects, methods provided herein can comprise analysis of chromosomal rearrangement, e.g., copy number variation, deficiencies, duplications, inversions, and translocations, and can further comprise determining pathology associated with the chromosomal rearrangement. Pathology associated with chromosomal rearrangement that the methods and systems provided herein are applicable to can include near all types of cancer and various types of genetic diseases, e.g., Wolf-Hirschhorn syndrome, Jacobsen syndrome, Charcot-Marie-Tooth disease type 1A, Angelman syndrome, Turner Syndrome, 22q11.2 deletion syndrome, Triple X Syndrome, Williams Syndrome, Cri du Chat Syndrome, Cat Eye Syndrome, 1q21.1 duplication syndrome, 15q13.3 microdeletion syndrome, 16p11.2 deletion syndrome, 17q23.1q23.2 microdeletion syndrome, 1q duplication syndrome, 1q21.1 microdeletion syndrome, 22q11.2 deletion syndrome, 22q11.2 duplication syndrome, 2q23.1 microdeletion syndrome, 2q37 deletion syndrome, 47 XXX syndrome, 47, XYY syndrome, 49, XXXXX syndrome, Diploid-triploid mosaicism, Distal chromosome 18q deletion syndrome, Emanuel syndrome, Kleefstra Syndrome, Koolen de Vries Syndrome, Mosaic monosomy 18, Nablus mask-like facial Syndrome, Pallister-Killian Mosaic Syndrome, Smith-Magenis Syndrome, Tetrasomy 9p Syndrome, Tetrasomy X Syndrome, Triploidy Syndrome, Trisomy 13 Syndrome, Trisomy 17 mosaicism, and Trisomy 2 mosaicism.

VIII. Classification of Cancer

Viral DNA integration breakpoint can be used as a basis for classification of cancer according to methods mentioned herein. In some cases, other classification of pathology, e.g., cancer, can also take advantage of the methods provided in the present disclosure.

Classification of cancer can comprise a presence or an absence of a cancer. Methods provided herein can be used to determination classification of any type of cancer, such as, but not limited to, bladder cancer, bone cancer, a brain tumor, breast cancer, carcinoma of cervix, colorectal cancer, esophageal cancer, gastrointestinal cancer, hematopoietic malignancy, head and neck squamous cell carcinoma, leukemia, liver cancer, lung cancer, lymphoma, myeloma, nasal cancer, nasopharyngeal cancer, oral cancer, oropharyngeal cancer, ovarian cancer, prostate cancer, sarcoma, stomach cancer, or thyroid cancer.

Classification of cancer can comprise a level of cancer or a stage of cancer. A level of cancer or a stage of cancer (e.g., Stage I, II, III, or IV) can refer to a size of tumor, a presence or an absence of metastasis, the total tumor burden of the body, and/or other measure of a severity of a cancer (e.g., recurrence of cancer). The level of cancer can be a number or other indicia, such as symbols, alphabet letters, and colors. The level can be zero. The level of cancer can also include premalignant or precancerous conditions (states) associated with mutations or a number of mutations.

Classification of cancer can also be used in various ways. In some instances, classification of cancer comprises progression of cancer or regression of cancer. In some instance, classification of cancer comprises prognostication or prediction of progression or regression of cancer with or without treatment of the cancer. For example, methods and systems as described herein can be used to determine if cancer is present in someone who is not known previously to have cancer. Assessment can investigate someone who has been diagnosed with cancer to monitor the progress of cancer over time, study the effectiveness of therapies or to determine the prognosis. In some cases, the prognosis can be expressed as the chance of a patient dying of cancer, or the chance of the cancer progressing after a specific duration or time, or the chance of cancer metastasizing.

Figure 6:
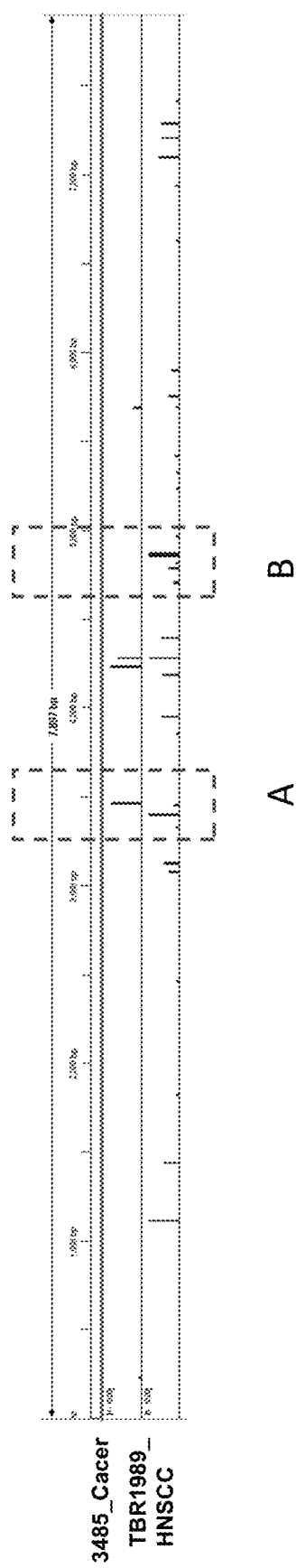
FIG. 6 shows distribution patterns of integration breakpoints in an HPV16 genome deduced from human-HPV chimeric fragments from samples from patients with carcinoma of cervix (Ca Cer) and HPV positive head and neck squamous cell carcinoma (HNSCC).

Classification of cancer, in some instances, comprises a type of cancer, for instance, carcinoma of cervix (CC) or head and neck squamous cell carcinoma (HNSCC). FIG. 6 shows distribution of viral integration breakpoints in HPV16 genome based on analysis of cell-free DNA from plasma samples of patients with carcinoma of cervix and HPV positive head and neck squamous cell carcinoma, respectively. As shown in the figure, there can be shared preferred integration breakpoints between carcinoma of cervix and HPV-positive head and neck squamous cell carcinoma (region A). On the other hand, there can also be preferred integration breakpoints characteristic of a certain type of cancer, for instance region B shows HNSCC-preferred integration breakpoints.

Viral integration breakpoints characteristic of certain classification of cancer, e.g., type of cancer, can be identified using methods provided herein; in some cases, in order to determine classification of cancer, similar methods can be applied to determine the viral integration breakpoints, where sequence reads of nucleic acid molecules from a biological sample are analyzed.

IX. Pathogen Integration: Viral Integration

Methods and systems provided herein can be used to detect to different types of viral integration that may exist in a host organism genome, such as mandatory integration. Mandatory integration into host organism genome can be an obligatory event during viral replication for some viruses, such as retroviridae, pseudoviridae, metaviridae, some myoviridae and siphoviridae. Integration of the viral DNA can result in permanent insertion of the viral genome into the host organism chromosomal DNA, referred as a provirus in the case of retroviruses or prophage in the case of prokaryotic viruses. Methods and systems provided herein can be used to detect occasional integration. Occasional integration may not be necessary during viral replication for some viruses, but can confer some advantages to the host/virus couple. Methods and systems provided herein can be used to detect endogenous viral elements (EVE). Some endogenous viruses can be integrated and "fossilized" into a host organism genome, through a rare and sometimes accidental process, including endogenous retroviruses, and rare RNA virus integration. One example of EVE includes endogenous retroviruses that become integrated in the germline. An integrated genome of endogenous retro-viruses can remain latent and be passively replicated along with the host organism genome and passed on to the cell's offspring. A host organism's environmental condition changes can however reactivate the virus leading to viral transcription and production of new infectious viruses (productive infection).

Methods and systems provided herein can be used to analyze DNA viruses and RNA viruses.

Methods and systems provided herein can be used to analyze integration of DNA viruses. The genome of DNA viruses can be a potential substrate for host organism genome integration, without the need for prior processing. Upon infection of a cell, a genome of DNA viruses can be translocated to the nucleus, where it can remain as an episome to ensure viral persistence or become integrated into a genome of the host cell.

Methods and systems provided herein can be used to investigate integration of Herpes viruses. Herpes viruses can be DNA enveloped viruses, and can be classified in three families based on their sequence phylogeny: α, β and γ herpes viruses. They can contain a linear double stranded DNA that is delivered in the nucleus upon viral entry and circularized. A herpes virus can remain episomal, e.g., as an extrachromosomal circular DNA. Some herpes viruses can integrate their genome into the host chromosomes. Examples of Herpes viruses include Epstein-Barr virus (EBV) and Human Herpes Virus-6 (HHV-6).

Methods and systems provided herein can be used to analyze integration of human papillomaviruses (HPV). HPV DNA can integrate into genome of host cells. DNA damage and agents that can induce DNA damage, e.g., double strand breaks (DSBs) can play a role in HPV integration.

Methods and systems provided herein can be used to analyze integration of Hepatitis B Virus (HBV). HBV can cause or play a role in the development of hepatocellular carcinoma. During acute infection, HBV can integrate its genome into the host chromosomes and present several similarities with retroviral integration.

Methods and systems provided herein can be used to analyze integration of Adeno-Associated Virus type 2 (AAV-2). The adeno-associated virus AAV can be a widespread virus classified among the parvoviridae family. Replication of AAV can be strictly conditioned by the presence in the same infected cell of helper viruses such as adenoviruses, human papillomaviruses (HPV) or herpes simplex viruses (HSV). In absence of helper viruses, AAV can integrate its genome in a site-specific way.

Methods and systems provided herein can be used to analyze integration of RNA viruses. The viral RNA genome of a retrovirus can be reverse transcribed into a linear double-strand DNA molecule (viral DNA intermediate), which can thus be the substrate for subsequent viral genome integration into the host genome. For retroviruses, integration can be a mandatory step for productive infection. The genome of other RNA viruses can also be identified in a host genome. In these cases, integration can occur incidentally, such as for lymphocytic choriomeningitis virus (LCMV). Methods and systems provided herein can also help elucidate the role of RNA virus integration in viral life cycle as well as pathology development in the host organism.

X. Viral Integration and Cancer

In some examples, the methods and systems provided herein can be used to determine a classification of cancer by determining viral integration.

In some cases, the methods and systems provided herein can be used to analyze tumor viruses (or oncoviruses), which can directly cause cancer in either experimental animals or humans. There are several families of tumor viruses, including, hepatitis B virus (liver cancer), papillomaviruses (cervical and other anogenital cancers), Epstein-Barr virus (Burkitt's lymphoma and nasopharyngeal carcinoma), Kaposi's sarcoma-associated herpesvirus (Kaposi's sarcoma), polyomavirus (Merkel cell carcinoma) and human T-cell lymphotropic virus (adult T-cell leukemia). Five of the six non-limiting families have DNA genomes and are referred to as DNA tumor viruses, and another family are the retroviruses, which have RNA genomes in virus particles but can replicate via synthesis of a DNA provirus in infected cells. In addition, HIV can be indirectly responsible for the cancers that develop in AIDS patients as a result of immunodeficiency, and hepatitis C virus (an RNA virus) can be an indirect cause of liver cancers resulting from chronic tissue damage.

Methods and systems provided herein can be used to analyze integration of HBV for determining HBV-associated conditions/diseases like hepatocellular carcinoma (HCC). HBVs can infect liver cells of several species, including ducks, woodchucks, squirrels, and humans. Infection with hepatitis B virus can result in acute liver damage. Hepatitis B virus infection can be common in parts of Asia and Africa, where it can be associated with up to a million cases of liver cancer annually (approximately 10% of worldwide cancer incidence). Cell transformation by hepatitis B virus can be mediated by a viral gene (called the X gene) that affects expression of a variety of cellular genes that drive abnormal cell proliferation and survival. In addition, the development of cancers induced by hepatitis B virus can be driven by the continual proliferation of liver cells that results from chronic tissue damage. Methods and systems provided herein can be used to diagnose, monitor, or prognosticate pathology associated with any genotype or serotype of Hepatitis B viruses, such as genotype F, E, A, B, C, and D, and various subtypes thereof.

HBV can be associated with HCC. HBV is a partially double-stranded DNA hepadnavirus with retroviral features. Integration of the HBV genome into a cellular genome can be present in over 85%-90% of HBV-related HCCs. However, the integrated form of HBV can be also present in non-tumor tissue of patients with chronic HBV infections. Integration of the HBV genome into hepatocytes can occur during persistent HBV infection and precede development of HCC. HBV integration can lead to the elevated expression of several cellular cancer-related genes, such as TERT, mixed-lineage leukemia 4 (MLL4) and CCNE1 (encoding cyclin E1). HBV integration can also be associated with early onset of HCC and poor outcomes.

Methods and systems provided herein can be used to determine papillomavirus integration profile to assess papillomavirus-associated conditions/diseases like cervical carcinoma. Papillomaviruses can be small DNA viruses (genomes of approximately 8 kb) that can induce both benign and malignant tumors in humans and a variety of other animal species. Approximately 60 different types of human papillomaviruses, which can infect epithelial cells of several tissues, have been identified. Some of these viruses can cause only benign tumors (such as warts), whereas others can be causative agents of malignant carcinomas, particularly cervical carcinoma, head and neck squamous cell carcinoma (HNSCC) and other anogenital cancers. Methods and systems provided herein can be used to differentiate different types of pathology, e.g., cancer, associated with HPVs. Methods and systems provided herein can also be used to analyze any type of papillomavirus, including HPV types 6, 11, 16, 18, 31, 33, 35, 39, 45, 51, 52, 56, 58, 59, 68, 73 and 82.

A subset of HPVs can infect the anogenital area, and within this subset, the individual types can be classified as either high risk or low risk. High-risk HPVs can cause cancerous lesions, while low-risk HPVs do not. A difference between high- and low-risk HPVs can be that high-risk HPVs show a greater tendency to integrate into the host genome, thereby causing high-grade lesions and cancer, while low-risk types can be preferentially maintained as extrachromosomal circular episomes. HPV can cause virtually all cases of cervical cancer, which can be the second most common cancer in women worldwide and the fourth most common cause of cancer death in women worldwide. HPV16, HPV18, HPV31 and HPV33 can account for 90% of all cases of cervical cancer. Among these high-risk HPVs, HPV type 16 is the most prevalent type and by itself can account for more than 50% of all cases of cervical cancer. High-risk HPV infection can also be associated with several other anogenital and oropharyngeal cancers. For example, it is thought to be responsible for more than 90% of anal cancers, 70% of vaginal and vulvar cancers, 60% of penile cancers and 63% of oropharyngeal cancers. 95% of patients with precancerous lesions of the cervix can harbor HPV, only a small fraction of these can eventually progress to invasive carcinoma. Three premalignant stages, cervical intraepithelial neoplasia (CIN)1, CIN2, and CIN3, can precede development of invasive carcinoma. CIN1 lesions can regress spontaneously, with only a few lesions progressing to CIN2/CIN3 and eventually to invasive carcinoma. Progression of cervical cancer in HPV-infected women can be tightly linked to integration status, and the frequency with which HPV is found integrated in cervical cancers can be consistently high. For example, 100% of HPV18-, 80% of HPV16- and 81% of HPV31-positive cancers can show viral integration. Methods and systems provided herein can be useful for prognosticating and monitoring cancer, e.g., cervical cancer by determining a HPV integration profile in subject.

Methods and systems provided herein can be used to determine herpesviruses integration profile to assess herpesviruses-associated conditions/diseases like nasopharyngeal cancer. Herpesviruses can be among the most complex animal viruses, with genomes of 100 to 200 kb. Several herpesviruses can induce tumors in animal species, including frogs, chickens, and monkeys. In addition, two members of the herpesvirus family, Kaposi's sarcoma-associated herpesvirus and Epstein-Barr virus, can be associated with human cancers. Kaposi's sarcoma-associated herpesvirus can play a critical role in the development of Kaposi's sarcomas, and Epstein-Barr virus can be implicated in several human malignancies, including Burkitt's lymphoma in some regions of Africa, B-cell lymphomas in AIDS patients and other immunosuppressed individuals, and nasopharyngeal carcinoma in China. Methods and systems provided herein can be used to analyze integration of different genera of herpesviruses like *Iltovirus, Proboscivirus, Cytomegalovirus, Mardivirus, Rhadinovirus, Macavirus, Roseolovirus, Simplexvirus, Scutavirus, Varicellovirus, Percavirus, Lymphocryptovirus*, and *Muromegalovirus*, human herpesviruses like Herpes simplex virus-1 (HSV-1), Herpes simplex virus-2 (HSV-2), Varicella zoster virus (VZV), Epstein-Barr virus (EBV), lymphocryptovirus, Cytomegalovirus (CMV), Roseolovirus, Herpes lymphotropic virus, and Kaposi's sarcoma-associated herpesvirus, (KSHV), and zoonotic herpesviruses like Cercopithecine herpesvirus-1, and Murid herpesvirus 68 (MHV-68).

EBV is a double-stranded DNA herpesvirus that can be primarily associated with Burkitt's lymphoma, nasopharyngeal carcinoma and several lymphoproliferative disorders. Burkitt's lymphoma can appear in three main clinical variants—the endemic, sporadic and immunodeficiency-associated variants. EBV can be detected in 96% of cases of endemic variant Burkitt's lymphoma involving the jaw, which is the most common malignancy of children in certain areas of central Africa. In contrast, EBV can rarely be associated with the sporadic variant of Burkitt's lymphoma, and the jaw is less commonly involved. EBV-associated Burkitt's lymphoma can be common in individuals lacking efficient T-cell function, such as AIDS patients or transplant recipients.

EBV can persist in an episomal state with multiple copies of circular DNA, but EBV integration into fragile sites of the host chromosome can be associated with partial deletion of the viral genome and can generate a region of enhanced chromatin instability in the host cell genome. This genome instability can induce the loss of host genes, such as BACH2, which can be a putative tumor suppressor gene, and this can contribute to lymphomagenesis.

In addition to Burkitt's lymphoma, EBV can also be associated with nasopharyngeal carcinoma (NPC). The undifferentiated form of NPC, classified by WHO as type III, can show consistent association with EBV worldwide, e.g., in particular areas of China and south-east Asia.

Methods and systems provided herein can be used to determine Merkel cell polyomavirus (MCV) integration profile to assess MCV-associated conditions/diseases like Merkel cell carcinoma (MCC). MCV can be a double-stranded DNA polyomavirus, which can be associated with MCC. These tumors can display MCV DNA in an integrated form within the tumor cell genomes in a clonal pattern. MCV infection and integration can contribute to clonal expansion of the tumor cells. The MCV genome can encode multiple splice variants of a tumor (T) antigen protein complex that targets several tumor suppressor proteins, such as pRB and p53. One of these splice variants, the large tumor antigen, can be mutated in MCV-positive MCC tumors cells, and this selective mutation can affect the cellular DNA damage response to prevent auto-activation of integrated virus replication, disrupt host genomic integrity and inhibit cellular proliferation MCV can frequently and selectively associate with MCV.

Members of one family of RNA viruses, the retroviruses, can cause cancer in a variety of animal species, including humans. For instance, retroviruses like human T-cell leukemia virus can cause adult T-cell leukemia, which can be common in parts of Japan, the Caribbean, and Africa. Different retroviruses can differ substantially in their oncogenic potential. Methods and systems provided herein can be used to differentiate pathology, e.g., cancer, associated with retroviruses. Methods and systems provided herein can be used to analyze any type of retroviruses, including exogenous retroviruses like members of genus *Alpharetrovirus, Betaretrovirus, Gammaretrovirus, Deltaretrovirus, Epsilonretrovirus, Lentiretrovirus*, and *Spumavirus*, and various endogenous retroviruses.

XI. Biological Sample

The biological sample used in methods as provided herein can include any tissue or material derived from a living or dead subject. A biological sample can be a cell-free sample. A biological sample can comprise a nucleic acid (e.g., DNA or RNA) or a fragment thereof. The nucleic acid in the sample can be a cell-free nucleic acid. A sample can be a liquid sample or a solid sample (e.g., a cell or tissue sample). The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. Stool samples can also be used. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). The biological sample can be treated to physically disrupt tissue or cell structure (e.g., centrifugation and/or cell lysis), thus releasing intracellular components into a solution which can further contain enzymes, buffers, salts, detergents, and the like which are used to prepare the sample for analysis.

Methods and systems provided herein can be used to analyze nucleic acid molecules in a biological sample. The nucleic acid molecules can be cellular nucleic acid molecules, cell-free nucleic acid molecules, or both. The cell-free nucleic acids used by methods as provided herein can be nucleic acid molecules outside of cells in a biological sample. The cell-free nucleic acid molecules can be present in various bodily fluids, e.g., blood, saliva, semen, and urine. Cell-free DNA molecules can be generated owing to cell death in various tissues that can be caused by health conditions and/or diseases, e.g., viral infection and tumor growth. Cell-free nucleic acid molecules can comprise sequences generated as a result of pathogen integration events.

Cell-free nucleic acid molecules, e.g., cell-free DNA, used in methods as provided herein can exist in plasma, urine, saliva, or serum. Cell-free DNA can occur naturally in the form of short fragments. Cell-free DNA fragmentation can refer to the process whereby high molecular weight DNA (such as DNA in the nucleus of a cell) are cleaved, broken, or digested to short fragments when cell-free DNA molecules are generated or released. Methods and systems provided herein can be used to analyze cellular nucleic acid molecules in some cases, for instance, cellular DNA from a tumor tissue, or cellular DNA from white blood cells when the patient has leukemia, lymphoma, or myeloma. Sample taken from a tumor tissue can be subject to assays and analyses according to some examples of the present disclosure.

XII. Subjects

Methods and systems provided herein can be used to analyze sample from a subject, e.g., organism, e.g., host organism. The subject can be any human patient, such as a cancer patient, a patient at risk for cancer, or a patient with a family or personal history of cancer. In some cases, the subject is in a particular stage of cancer treatment. In some cases, the subject can have or be suspected of having cancer. In some cases, whether the subject has cancer is unknown.

A subject can have any type of cancer or tumor. In an example, a subject can have nasopharyngeal cancer, or cancer of the nasal cavity. In another example, a subject can have oropharyngeal cancer, or cancer of the oral cavity. Non-limiting examples of cancer can include, but are not limited to, adrenal cancer, anal cancer, basal cell carcinoma, bile duct cancer, bladder cancer, cancer of the blood, bone cancer, a brain tumor, breast cancer, bronchus cancer, cancer of the cardiovascular system, cervical cancer, colon cancer, colorectal cancer, cancer of the digestive system, cancer of the endocrine system, endometrial cancer, esophageal cancer, eye cancer, gallbladder cancer, a gastrointestinal tumor, hepatocellular carcinoma, kidney cancer, hematopoietic malignancy, laryngeal cancer, leukemia, liver cancer, lung cancer, lymphoma, melanoma, mesothelioma, cancer of the muscular system, Myelodysplastic Syndrome (MDS), myeloma, nasal cavity cancer, nasopharyngeal cancer, cancer of the nervous system, cancer of the lymphatic system, oral cancer, oropharyngeal cancer, osteosarcoma, ovarian cancer, pancreatic cancer, penile cancer, pituitary tumors, prostate cancer, rectal cancer, renal pelvis cancer, cancer of the reproductive system, cancer of the respiratory system, sarcoma, salivary gland cancer, skeletal system cancer, skin cancer, small intestine cancer, stomach cancer, testicular cancer, throat cancer, thymus cancer, thyroid cancer, a tumor, cancer of the urinary system, uterine cancer, vaginal cancer, or vulvar cancer. The lymphoma can be any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The leukemia can be any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia. In some cases, the cancer patient does not have a particular type of cancer. For example, in some instances, the patient can have a cancer that is not breast cancer.

Examples of cancer include cancers that cause solid tumors as well as cancers that do not cause solid tumors. Furthermore, any of the cancers mentioned herein can be a primary cancer (e.g., a cancer that is named after the part of the body where it first started to grow) or a secondary or metastatic cancer (e.g., a cancer that has originated from another part of the body).

A subject diagnosed by any of the methods described herein can be of any age and can be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). A particular class of patients that can benefit can be patients over the age of 40. Another particular class of patients that can benefit can be pediatric patients. Furthermore, a subject diagnosed by any of the methods or compositions described herein can be male or female.

In some embodiments, a method of the present disclosure can detect a tumor or cancer in a subject, wherein the tumor or cancer has a geographic pattern of disease. In an example, a subject can have an EBV-related cancer (e.g., nasopharyngeal cancer), which is prevalent in South China (e.g., Hong Kong SAR). In another example, subject can have an HPV-related cancer (e.g., oropharyngeal cancer), which can be prevalent in the United States and Western Europe. In yet another example, a subject can have a Human T-lymphotrophic virus-1 (HTLV-1)-related cancer (e.g., adult T-cell leukemia/lymphoma), which can be prevalent in southern Japan, the Caribbean, central Africa, parts of South America, and in some immigrant groups in the southeastern United States.

Any of the methods disclosed herein can also be performed on a non-human subject, such as a laboratory or farm animal, or a cellular sample derived from an organism disclosed herein. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

XIII. Computer System

Any of the methods disclosed herein can be performed and/or controlled by one or more computer systems. In some examples, any step of the methods disclosed herein can be wholly, individually, or sequentially performed and/or controlled by one or more computer systems. Any of the computer systems mentioned herein can utilize any suitable number of subsystems. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems can be interconnected via a system bus. Additional subsystems include a printer, keyboard, storage device(s), and monitor that is coupled to display adapter. Peripherals and input/output (I/O) devices, which couple to I/O controller, can be connected to the computer system by any number of connections known in the art such as an input/output (I/O) port (e.g., USB, FireWire®). For example, an I/O port or external interface (e.g., Ethernet, Wi-Fi, etc.) can be used to connect computer system to a wide area network such as the Internet, a mouse input device, or a scanner. The interconnection via system bus allows the central processor to communicate with each subsystem and to control the execution of a plurality of instructions from system memory or the storage device(s) (e.g., a fixed disk, such as a hard drive, or optical disk), as well as the exchange of information between subsystems. The system memory and/or the storage device(s) can embody a computer readable medium. Another subsystem is a data collection device, such as a camera, microphone, accelerometer, and the like. Any of the data mentioned herein can be output from one component to another component and can be output to the user.

A computer system can include a plurality of the same components or subsystems, e.g., connected together by external interface or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Figure 8:
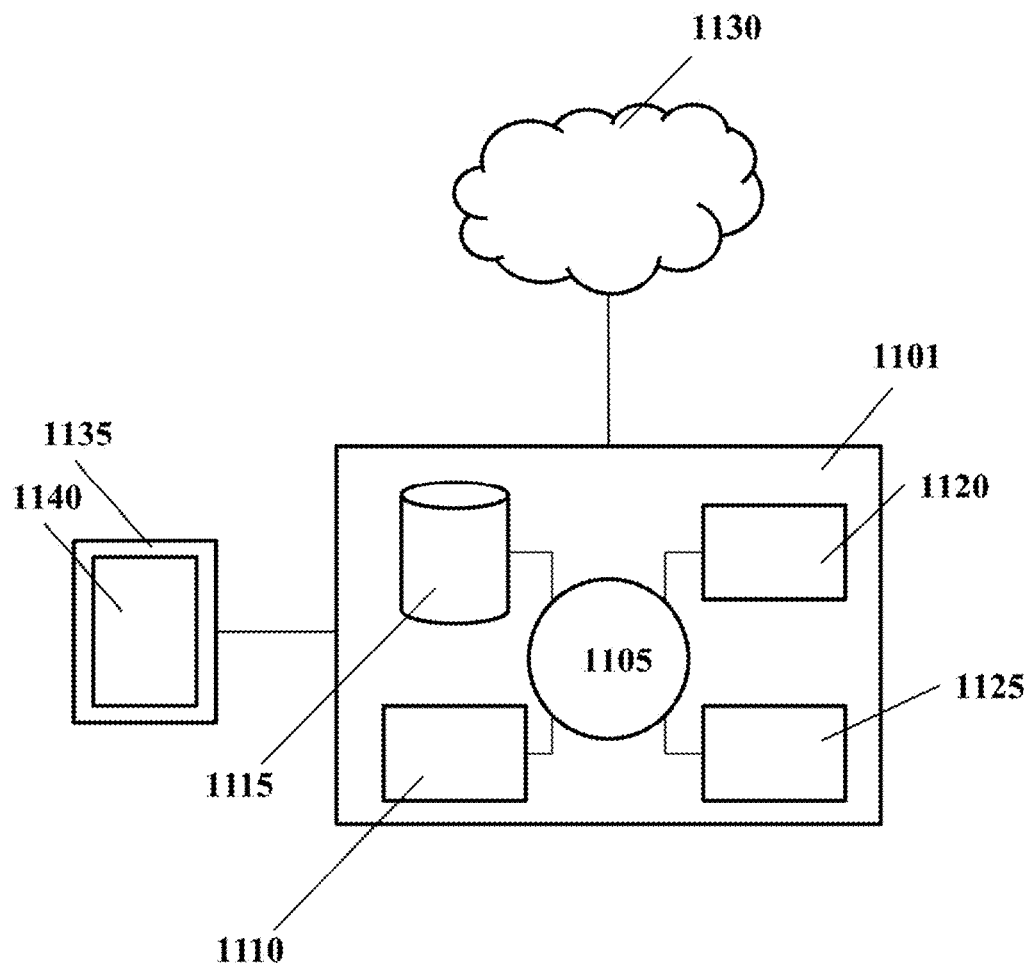
FIG. 8 shows a computer control system that may be programmed or otherwise configured to implement methods provided herein.

The present disclosure provides computer control systems that are programmed to implement methods of the disclosure. FIG. 8 shows a computer system 1101 that is programmed or otherwise configured to detect a chimeric nucleic acid fragment, or to determine a pathogen integration profile in a nucleic acid molecule, or to determine a classification of pathology as described herein. The computer system 1101 can implement and/or regulate various aspects of the methods provided in the present disclosure, such as, for example, controlling sequencing of the nucleic acid molecules from a biological sample, performing various steps of the bioinformatics analyses of sequencing data as described herein, integrating data collection, analysis and result reporting, and data management. The computer system 1101 can be an electronic device of a user or a computer system that is remotely located with respect to the electronic device. The electronic device can be a mobile electronic device.

The computer system 1101 includes a central processing unit (CPU, also "processor" and "computer processor" herein) 1105, which can be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet. The network 1130 in some cases is a telecommunication and/or data network. The network 1130 can include one or more computer servers, which can enable distributed computing, such as cloud computing. The network 1130, in some cases with the aid of the computer system 1101, can implement a peer-to-peer network, which may enable devices coupled to the computer system 1101 to behave as a client or a server.

The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some cases, the circuit is an application specific integrated circuit (ASIC).

The storage unit 1115 can store files, such as drivers, libraries and saved programs. The storage unit 1115 can store user data, e.g., user preferences and user programs. The computer system 1101 in some cases can include one or more additional data storage units that are external to the computer system 1101, such as located on a remote server that is in communication with the computer system 1101 through an intranet or the Internet.

The computer system 1101 can communicate with one or more remote computer systems through the network 1130. For instance, the computer system 1101 can communicate with a remote computer system of a user (e.g., a Smart phone installed with application that receives and displays results of sample analysis sent from the computer system 1101). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1101 via the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 can include or be in communication with an electronic display 1135 that comprises a user interface (UI) 1140 for providing, for example, results of sample analysis, such as, but not limited to graphic showings of pathogen integration profile, genomic location of pathogen integration breakpoints, classification of pathology (e.g., type of disease or cancer and level of cancer), and treatment suggestion or recommendation of preventive steps based on the classification of pathology. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1105. The algorithm can, for example, control sequencing of the nucleic acid molecules from a sample, direct collection of sequencing data, analyzing the sequencing data, or determining a classification of pathology based on the analyses of the sequencing data.

Figure 9:
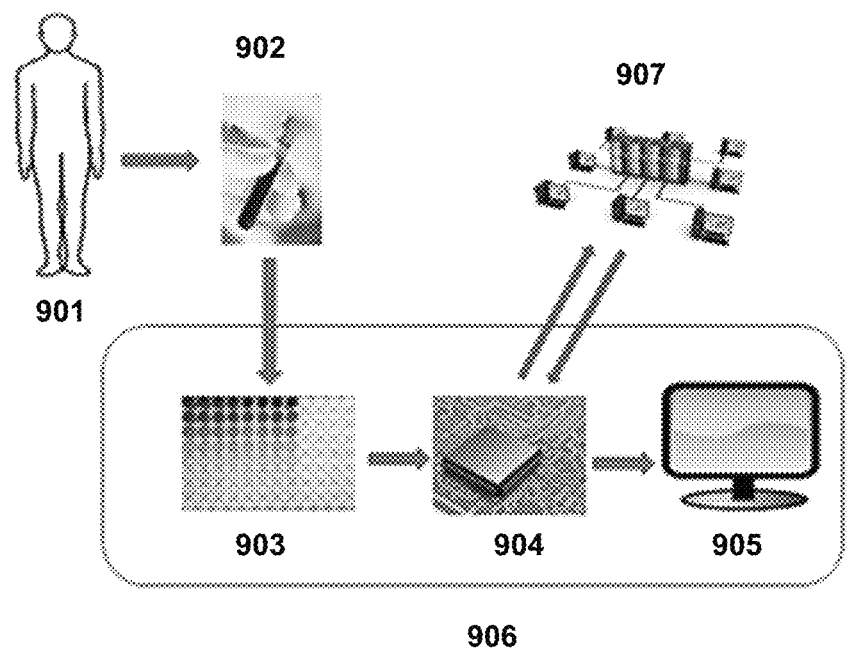
FIG. 9 shows a diagram of the methods and systems as disclosed herein.

In some cases, as shown in FIG. 9, a sample 902 may be obtained from a subject 901, such as a human subject. A sample 902 may be subjected to one or more methods as described herein, such as performing an assay. In some cases, an assay may comprise hybridization, amplification, sequencing, labeling, epigenetically modifying a base, or any combination thereof. One or more results from a method may be input into a processor 904. One or more input parameters such as a sample identification, subject identification, sample type, a reference, or other information may be input into a processor 904. One or more metrics from an assay may be input into a processor 904 such that the processor may produce a result, such as a classification of pathology (e.g., diagnosis) or a recommendation for a treatment. A processor may send a result, an input parameter, a metric, a reference, or any combination thereof to a display 905, such as a visual display or graphical user interface. A processor 904 may (i) send a result, an input parameter, a metric, or any combination thereof to a server 907, (ii) receive a result, an input parameter, a metric, or any combination thereof from a server 907, (iii) or a combination thereof.

Aspects of the present disclosure can be implemented in the form of control logic using hardware (e.g., an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments described herein using hardware and a combination of hardware and software.

Any of the software components or functions described in this application can be implemented as software code to be executed by a processor using any suitable computer language such as, for example, Java, C, C++, C#, Objective-C, Swift, or scripting language such as Perl or Python using, for example, conventional or object-oriented techniques. The software code can be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium can be any combination of such storage or transmission devices.

Such programs can also be encoded and transmitted using carrier signals adapted for transmission via wired, optical, and/or wireless networks conforming to a variety of protocols, including the Internet. As such, a computer readable medium can be created using a data signal encoded with such programs. Computer readable media encoded with the program code can be packaged with a compatible device or provided separately from other devices (e.g., via Internet download). Any such computer readable medium can reside on or within a single computer product (e.g., a hard drive, a CD, or an entire computer system), and can be present on or within different computer products within a system or network. A computer system can include a monitor, printer, or other suitable display for providing any of the results mentioned herein to a user.

Any of the methods described herein can be totally or partially performed with a computer system including one or more processors, which can be configured to perform the steps. Thus, embodiments can be directed to computer systems configured to perform the steps of any of the methods described herein, with different components performing a respective step or a respective group of steps. Although presented as numbered steps, steps of methods herein can be performed at a same time or in a different order. Additionally, portions of these steps can be used with portions of other steps from other methods. Also, all or portions of a step can be optional. Additionally, any of the steps of any of the methods can be performed with modules, units, circuits, or other approaches for performing these steps.

XIV. Other Embodiments

The section headings used herein are for organizational purposes only and are not to be construed as limiting the subject matter described.

It is to be understood that the methods described herein are not limited to the particular methodology, protocols, subjects, and sequencing techniques described herein and as such can vary. It is also to be understood that the terminology used herein is for the purpose of describing particular embodiments only, and is not intended to limit the scope of the methods and compositions described herein, which will be limited only by the appended claims. While some embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

XV. Examples

The following examples are offered by way of illustration, not by way of limitation.

Example 1. Analysis of HPV DNA Integration

This example tested exemplary approaches for determining HPV integration breakpoints by analyzing sequence reads of cell-free DNA from plasma sample. The example also examined different HPV integration profiles in samples of patients with cervical carcinoma and HPV-associated head and neck squamous cell carcinoma, as well as EBV integration profile in samples of patients with EBV infection.

Plasma samples from patients with HPV infection were collected and processed. Cell-free DNA molecules in the plasma samples were then collected and subject to paired-end sequencing. In the paired-end sequencing data, sequence reads from Type A and Type B human-HPV chimeric fragments as illustrated in FIG. 2 were selected.

To identify human-HPV chimeric DNA in the cell-free DNA samples, sequence reads obtained were aligned to a reference human genome and a reference HPV genome using SOAP alignment tool. Type A human-HPV chimeric fragment read pairs were identified by searching for read pairs (pairs of sequence reads obtained from the two ends of the same plasma cell-free DNA molecule) with one read mapped to the reference human genome and the other read mapped to the reference HPV genome. Type A chimeric fragments with the same start and end outer coordinates were removed as suspected PCR duplicates. All remaining Type A chimeric reads were then overlaid to group nucleotide coordinates that are overlapping or are adjacent to each other in the human and HPV sequences to identify candidate integration regions. Each candidate integration region on the human genome would have one or more corresponding candidate integration region(s) on the HPV genome, and vice versa. Adjacent human reads within a distance of 300 bases are grouped into one candidate integration region, and adjacent HPV reads within a distance of 300 bases are grouped into one candidate integration region (e.g., as illustrated in FIG. 3A). Any human sequence read whose distance from its nearest neighboring sequence read is more than 300 bases was not included in the same candidate integration region, and any HPV Human sequence read whose distance from its nearest neighboring sequence read is more than 300 bases apart was not included in the same candidate integration region. In this example, in each human-HPV candidate integration regions, there must be at least two human-HPV chimeric fragments that are not PCR duplicates.

The unmapped reads from the first alignment were then realigned to human and HPV genome using Bowtie2 with the local alignment function with a default minimum mapping length of 22 bases. Then their possible mapping positions were searched in the candidate integration regions suggested by Type A chimeric fragments. A minimum mapping length of 4 bases was then chosen to map unmapped part of partially mapped reads to corresponding integration candidate region with a minimum mapping length of 4 bp. Thus, human-HPV chimeric reads in Type B fragment read pairs were identified within candidate integration regions to determine the potential integration breakpoints. Within a candidate integration region, expected strand orientation for the human-HPV chimeric reads were inferred by the strand information of the Type A chimeric fragment read pairs that were used for constructing the candidate integration regions. Only the mapping position of the short sequence anchor being within 100 bp distance of the potential breakpoint was considered as a putative hit for the integration breakpoint. These reads were regarded as the chimeric reads covering the integration breakpoint.

Human-HPV chimeric reads whose mate reads are not compatible with the library insert sizes and mapping orientations were further excluded. Next, candidate integration sites with a Diversity Score below 4 were excluded. The remaining integration breakpoints were regarded as from the actual HPV integration events. Table 1 summarizes the analysis of HPV integration breakpoints with or without Diversity Score filtering with samples from patients with cervical carcinoma and HNSCC.

Similar analyses were performed for EBV integration breakpoints with plasma samples from nasopharyngeal cancer (NPC) patients with EBV infection. The analyses of EBV integration breakpoints with or without Diversity Score filtering are summarized in Table 2.

FIG. 6 shows distribution of viral integration breakpoints in HPV16 genome, based on analysis of plasma cell-free DNA from patients with carcinoma of cervix and HPV positive head and neck squamous cell carcinoma, respectively. As shown in the figure, there were shared preferred integration breakpoints between carcinoma of cervix and HPV-positive head and neck squamous cell carcinoma (region A). On the other hand, there were also preferred integration breakpoints characteristic of a certain type of cancer, for instance region B shows HNSCC-preferred integration breakpoints.

TABLE 1

Summary of HPV integration analysis

| Type | Sample | Total No. of Candidate Regions | Without Diversity Score Filtering | | Diversity Score >= 4 | |
|---|---|---|---|---|---|---|
| | | | No. of chimeric reads | No. of breakpoints | No. of chimeric reads | No. of breakpoints |
| Cervical Carcinoma | 3485 | 458 | 28317 | 1054 | 10723 | 6 |
| | C-788 | 43 | 77 | 26 | 0 | 0 |
| | C-801 | 2 | 0 | 0 | 0 | 0 |
| | C-819 | 2 | 0 | 0 | 0 | 0 |
| | C-822 | 5 | 0 | 0 | 0 | 0 |
| | C-877 | 9 | 0 | 0 | 0 | 0 |

TABLE 1-continued

Summary of HPV integration analysis

| Type | Sample | Total No. of Candidate Regions | Without Diversity Score Filtering | | Diversity Score >= 4 | |
|---|---|---|---|---|---|---|
| | | | No. of chimeric reads | No. of breakpoints | No. of chimeric reads | No. of breakpoints |
| HNSCC | TBR_1019 | 8 | 0 | 0 | 0 | 0 |
| | TBR1245 | 1 | 0 | 0 | 0 | 0 |
| | TBR1988 | 3 | 0 | 0 | 0 | 0 |
| | TBR1989 | 12414 | 234667 | 96039 | 1521 | 41 |
| | TBR2175 | 22 | 9 | 3 | 0 | 0 |

TABLE 2

Summary of EBV integration analysis

| Sample | Total No. of Candidate Regions | Without Diversity Score Filtering | | Diversity Score >=4 | |
|---|---|---|---|---|---|
| | | No. of chimeric reads | No. of breakpoints | No. of chimeric reads | No. of breakpoints |
| TBR1358 | 1 | 1 | 1 | 0 | 0 |
| TBR1378 | 45 | 117 | 59 | 0 | 0 |
| TBR1390 | 188 | 1106 | 410 | 0 | 0 |
| TBR1344 | 3153 | 33405 | 10426 | 0 | 0 |
| TBR1360 | 913 | 14293 | 3550 | 0 | 0 |
| TBR1379 | 1334 | 22027 | 4932 | 0 | 0 |

Example 2. Analysis of HPV DNA Integration Index

This example examined HPV DNA integration index in cell-free DNA from plasma sample of patient with carcinoma of cervix and HNSCC.

To analyze cell-free DNA fragments in plasma which show HPV integration into the human chromosomes within the cancer genome, paired-end sequencing was performed with these cell-free DNA fragments. A protocol of paired-end sequencing which reads 75 nucleotides from each end of cell-free DNA fragments was used. Cell-free DNA fragments with all the 75 nucleotides of either one read sequence being mapped to the HPV genome and the other read sequence being mapped to the human genome were counted as human-HPV chimeric fragments. Cell-free DNA fragments with both reads in the paired-end sequencing being mapped to the HPV genome were counted as the plasma HPV reads. Samples from 11 patients with carcinoma of cervix were analyzed.

TABLE 3

Plasma cell-free human-HPV fragment DNA in CC samples

| Sample | HPV type | No. of reads of human-HPV chimeric fragments | No. of plasma HPV reads |
|---|---|---|---|
| 3276 | HPV16 | 12 | 62 |
| 3485 | HPV16 | 180892 | 2316992 |
| 3499 | HPV16 | 4 | 72 |
| 3542 | HPV16 | 5 | 50 |
| 3581 | HPV16 | 12 | 90 |
| C-788 | HPV16 | 108848 | 1659430 |
| C-801 | HPV16 | 10531 | 153660 |
| C-803 | HPV16 | 3271 | 53544 |
| C-819 | HPV16 | 1466 | 20806 |
| C-822 | HPV16 | 2461 | 59532 |
| C-877 | HPV16 | 37126 | 616528 |

Figure 7:
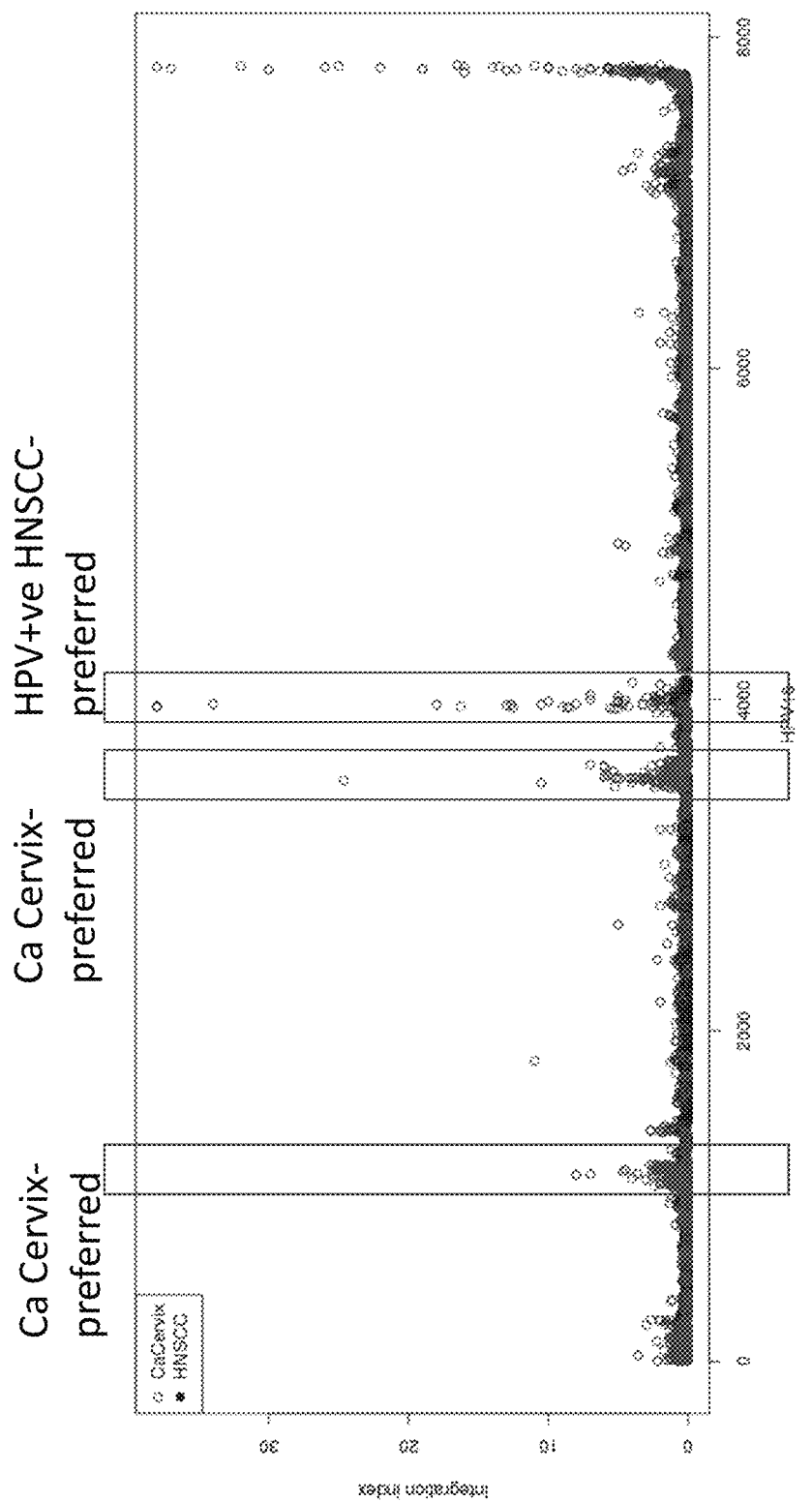
FIG. 7 shows integration index across HPV genome determined from cell-free DNA fragments from samples of patients with carcinoma of cervix (Ca Cervix-) and HPV positive HNSCC (HPV+veSCC).

Using the same protocol for defining plasma cell-free human-HPV chimeric fragments, genomic position of plasma cell-free human-HPV chimeric fragments was analyzed in sample from one patient with carcinoma of cervix (CaCx3485) and sample from one patient with HPV positive head and neck squamous cell carcinoma (HPV+ve HNSCC) (TBR1989). In FIG. 7, each dot represents the exact ending position of plasma cell-free DNA fragments with HPV integration. The integration index refers to the odds ratio of the ending position of plasma cell-free DNA fragments with HPV integration compared to plasma HPV fragments (both read 1 and 2 mapped to HPV genome). The higher the integration index, the more likely the position where those DNA fragment reads with HPV integration end. A difference was observed in the preferred ending positions for plasma cell-free DNA reads with HPV integration across the HPV genome between the patients with carcinoma of cervix and HPV-positive HNSCC (HPV+ve HNSCC).

Example 3. Comparison with Public Software ViFi

In this example, performance of an exemplary algorithm in HPV integration detection according to the present disclosure was compared with ViFi (Nguyen et al., Nucleic Acids Res. 2018 Apr. 20; 46(7):3309-3325. doi: 10.1093/nar/gky180), a software that detects viral integration sites through a combination of phylogenetic methods and reference-based reads alignment. Simulation dataset with artificially constructed integration sites, as well as biological data of tissue samples and paired plasma samples from 26 cervical intraepithelial neoplasia (CIN), 26 cervical cancer (CaCx) and 7 head and neck squamous-cell carcinoma (HNSCC) patients were used to evaluate the detection performance of the exemplary algorithm and ViFi. The integration sites identified by the exemplary algorithm were further verified by PCR amplification and Sanger sequencing.

Method

Public Software: ViFi

ViFi was downloaded from github.com/namphuonNiFi and run under its default setting and default parameters on both the simulation data and the real sequencing data of the tissue and plasma samples from cervical cancer and HNSCC patients in fastq format.

Simulation Dataset

To evaluate the exemplary algorithm, 32,500 chimeric fragments, including both Type A and Type B fragments, were constructed in silico to artificially generate 500 HPV integration sites. These in silico constructed chimeric fragments were then mixed with real sequencing reads of one human cervical cancer plasma sample. The sequencing reads of the human cervical cancer plasma sample contained no HPV integration sites. The detection performance of the exemplary algorithm was compared with ViFi (Nguyen et al., Nucleic Acids Res. 2018 Apr. 20; 46(7):3309-3325. doi: 10.1093/nar/gky180).

Sequencing Data of Tissue and Plasma DNA from Cervical Cancer, HNSCC Patients and NPC Patients To explore the HPV16 integration landscape in HPV associated tumors, 26 plasma samples from cervical cancer and 7 tissue samples and paired plasma samples from HNSCC patients were sequenced. Both the exemplary algorithm and ViFi were applied for the detection of HPV integration sites in these samples. 6 plasma samples from nasopharyngeal carcinoma (NPC) patients were also sequenced for the detection of Epstein-Barr virus (EBV) integration events in human genome.

Results

Simulated Data

Figure 10:
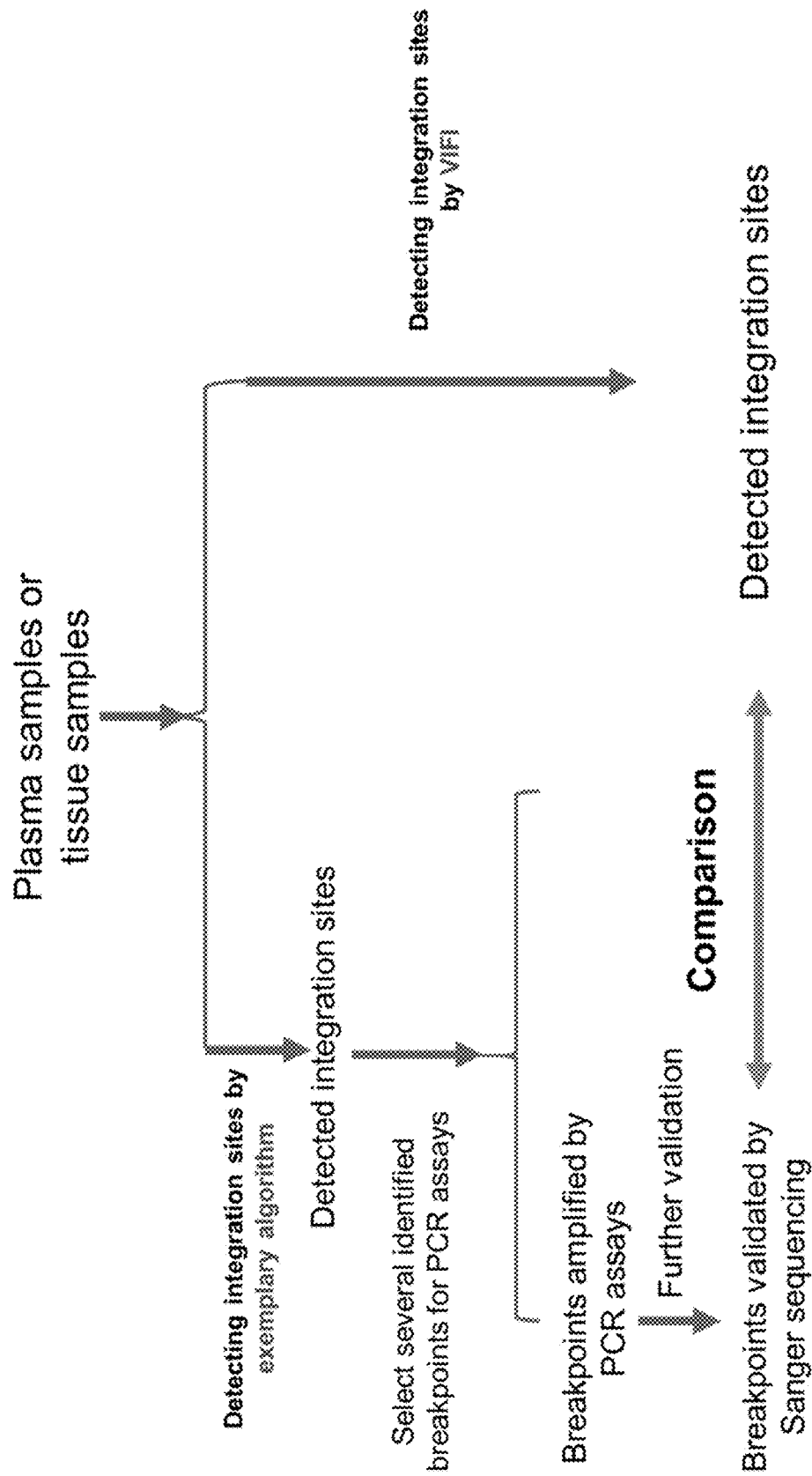
FIG. 10 is a diagram illustrating the workflow for the comparison of detection rate between an exemplary algorithm and VIFI on simulation dataset.
Figure 11:
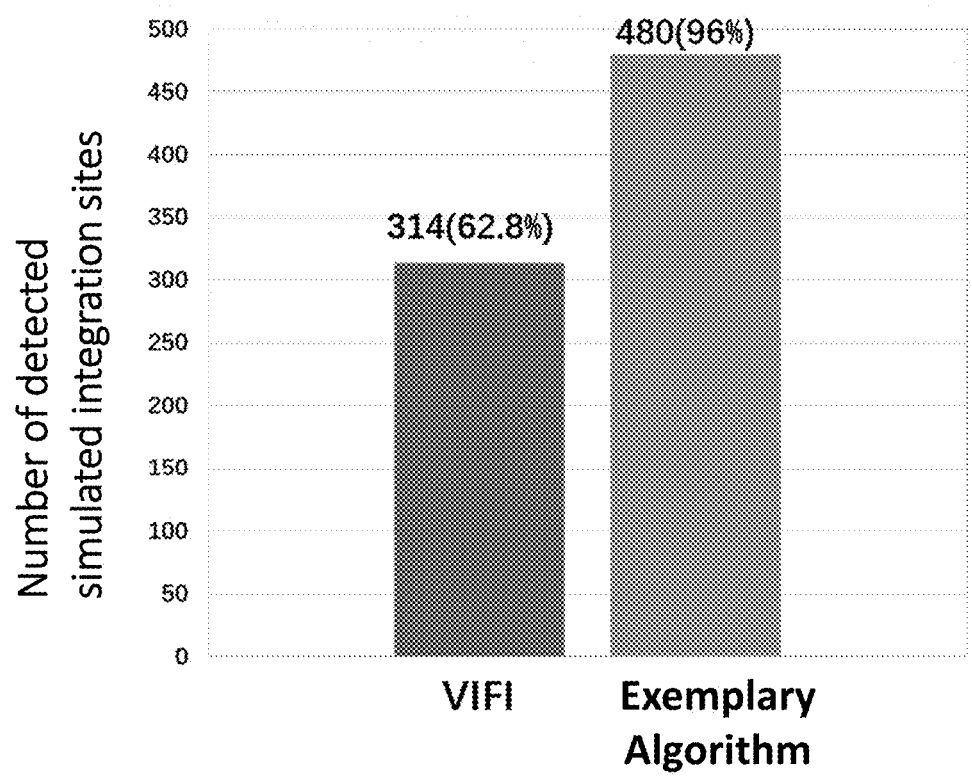
FIG. 11 is a chart summarizing the comparison of detection rate between an exemplary algorithm and VIFI on simulation dataset.

To directly evaluate the detection performance of the exemplary algorithm and compare it to ViFi, 500 integration sites were artificially constructed as supported by corresponding chimeric fragments. Both the exemplary algorithm and ViFi were run on this simulation dataset and compared on the detection rate (FIG. 10). As shown in FIG. 11, ViFi detected 314 simulated integration regions among total 500 sites, with a detection rate of only 62.8%. However, using the exemplary algorithm, 480 simulated integration sites were accurately identified, including not only the integration regions but also the exact breakpoints, with a significant higher detection rate of 96%. These results showed that the exemplary algorithm has a higher accuracy in detecting integration sites in simulation dataset compared with ViFi.

Breakpoints Identified from Plasma DNA

The exemplary algorithm was run on the plasma DNA sequencing data of the 26 CIN, 26 cervical cancer and 7 HNSCC patients, in which 6 cervical cancer and 5 HNSCC plasma samples were shown to have at least 1 candidate integration region (FIG. 12). After filtering with a cutoff diversity score of 4, 1 cervical cancer (CaCx3485) and 1 HNSCC (TBR1989) case remained with 6 and 41 breakpoints identified by the exemplary algorithm, respectively (FIG. 12). Among these breakpoints, 6 and 9 breakpoints were selected for experiment validation in the cervical cancer and HNSCC cases, respectively, among which, 1 breakpoint in the cervical cancer case and 3 breakpoints in the HNSCC case were validated by a PCR assay. Meanwhile, ViFi was run on the same plasma sequencing dataset to compare with the exemplary algorithm. ViFi only identified one case, CaCx3485, with 491 putative integration breakpoints initiated by HPV16. Nevertheless, none of the breakpoints identified by ViFi overlapped with any of the breakpoints identified by the exemplary algorithm with a diversity score above 4, including the breakpoint validated in this case.

Breakpoints Identified from Tumor Tissue DNA

In addition, 7 tissue samples of the HNSCC patients aforementioned were sequenced. Diversity score of 4 was used as a cutoff in the exemplary algorithm. FIG. 13 shows that 4 out of the 5 samples contained at least one candidate integration region with at least one identified integration breakpoint that remained after application of the cutoff score. These breakpoints were further validated experimentally by PCR and Sanger sequencing.

There were in total 56 integration breakpoints identified from 4 HNSCC samples with diversity score ≥4 (FIG. 13). After merging the 26 breakpoints with close junctional sites (1-5 bp), the total number of breakpoints was reduced to 43. PCR assays were designed for 32 of the breakpoints, flanking the integration sites in the amplicon with size less than 200 bp. 23 of the breakpoints have been successfully amplified from the tissue DNA of the corresponding samples, showing expected amplicon sizes and among which, 22 breakpoints were further validated by Sanger sequencing. Therefore, based on our algorithm, the overall validation rate of breakpoints with diversity score ≥4 is 69.0% (22/32).

If the diversity score cutoff was set as 9, 24 breakpoints were targeted by designed PCR assays, in which 22 of which have been successfully amplified and validated by Sanger sequencing. Hence, the overall validation rate drastically improved to 91.7% (22/24) after the cutoff diversity score was raised from 4 to 9.

In summary, the performance of the exemplary algorithm was compared with that of ViFi using the tissue sequencing data. No breakpoint was identified by ViFi in any tissue sample.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein can be employed in practicing the disclosure. It is intended that the following claims define the scope of the disclosure and that methods and structures within the scope of these claims and their equivalents be covered thereby.

What is claimed is:

1. A method of identifying an integration breakpoint position in a genome of a human subject suspected to comprise a pathogen integration at an unknown genomic location, the method comprising:
   (a) sequencing cell-free nucleic acid fragments from a biological sample of the subject to produce paired-end sequencing reads;
   (b) aligning the paired-end sequencing reads to (i) a reference human genome, and (ii) a reference genome of the pathogen, wherein the aligning uses an alignment algorithm:
   (c) identifying one or more chimeric read pairs, wherein a chimeric read pair comprises (i) a first read that aligns to the reference genome of the pathogen and (ii) a second read that aligns to the reference human genome; and
   (d) identifying the unknown genomic location in the genome of the subject within 500 nucleotides of the second read of the one or more chimeric read pairs as the integration breakpoint position.

2. A method of identifying an integration breakpoint position in a genome of an organism comprising a pathogen integration, the method comprising:
   (a) obtaining a plurality of paired-end sequencing reads for cell-free nucleic acid molecules from a biological sample of the organism;
   (b) performing a first alignment of the plurality of paired end sequencing reads, with a first alignment algorithm, wherein the first alignment identifies one or more Type A fragments comprising (i) a first sequence read of a read pair that aligns to a reference genome of the organism, and (ii) a second sequence read of the read pair that aligns to a reference genome of the pathogen;

(c) identifying one or more candidate integration regions in the reference genome of the organism, wherein a candidate integration region is identified as being within 500 bases of where one of the first sequence reads of a Type A fragment aligns;

(d) performing a second alignment of a subset of the plurality of paired end sequencing reads against the one or more candidate integration regions with a second alignment algorithm, wherein the second alignment identifies one or more Type B fragments comprising (i) a first sequence read of a read pair that aligns to the reference genome of the organism or the reference genome of the pathogen, and (ii) a second sequence read comprising a first portion that aligns to one of the one or more candidate integration regions and a second portion that aligns to the reference genome of the pathogen; and (e) identifying the integration breakpoint position at a junction formed by the first portion and the second portion of the second sequence read of one of the one or more Type B fragments.

3. The method of claim 2, wherein identifying the candidate integration region further comprises performing a local alignment of unmapped reads from the first alignment.

4. The method of claim 2, further comprising sequencing the cell-free nucleic acid molecules from the biological sample to produce the paired-end sequencing reads.

5. The method of claim 3, wherein the local alignment uses a first sequence stretch length, and the second alignment uses a second sequence stretch length that is shorter than the first sequence stretch length.

6. The method of claim 2, wherein the first alignment comprises aligning at least 20 consecutive nucleotides of the second sequence read to the reference genome of the pathogen, and aligning at least 20 consecutive nucleotides of the first sequence read to the reference genome of the organism.

7. The method of claim 4, further comprising amplifying cell-free nucleic acid molecules from a second biological sample of the organism, wherein the amplifying comprises amplification of cell-free nucleic add molecules comprising the integration breakpoint with a first primer complementary to a first target sequence in the genome of the pathogen, and a second primer complementary to a second target sequence in the genome of the organism.

8. The method of claim 2, wherein the pathogen comprises a virus.

9. The method of claim 8, wherein the virus comprises Epstein-Barr Virus DNA, human papillomavirus DNA, Hepatitis B Virus DNA, Hepatitis C Virus nucleic acids, or fragments thereof.

10. The method of claim 2, wherein the organism is a human.

11. The method of claim 2, wherein the biological sample is plasma, serum, or urine.

12. The method of claim 1, wherein step (c) further comprises:
identifying a plurality of different chimeric read pairs of cell-free nucleic acid molecules from the biological sample comprising a same potential integration breakpoint.

13. The method of claim 12, wherein step (d) further comprises:
determining a strand orientation of a first sequence read and a second sequence read of each of the plurality of different chimeric read pairs;
filtering out a chimeric read pair comprising a strand orientation of the first sequence read and the second sequence read inconsistent with a strand orientation of the first sequence read and the second sequence read of a majority of the chimeric read pairs; and
after the filtering out, detecting the integration breakpoint based on the remaining chimeric read pairs.

14. The method of claim 12, wherein step (d) further comprises:
assessing a variability in lengths of sequences of sequence reads of the sequence read pairs aligning to a genomic region flanking the potential integration breakpoint.

15. The method of claim 12, wherein the identifying the plurality of different chimeric read pairs comprises:
identifying human-pathogen chimeric sequence read pairs generated from paired-end sequencing of the cell-free nucleic acid molecules from the biological sample that comprise a first sequence read aligning to the reference human genome and a second sequence read aligning to the reference genome of the pathogen, thereby identifying Type A human-pathogen chimeric sequence read pairs;
grouping, from the Type A human-pathogen chimeric sequence read pairs, Type A human-pathogen chimeric sequence read pairs comprising first sequence reads that are overlapping or separated within a predetermined distance in the reference human genome, and second sequence reads that are overlapping or separated within a predetermined distance in the reference genome of the pathogen, thereby identifying a human-pathogen candidate integration region in the reference genomes; and
identifying human-pathogen chimeric sequence read pairs generated from paired-end sequencing of the cell-free nucleic acid molecules from the biological sample that comprise a first sequence read aligning to the human-pathogen candidate integration region and a second sequence read comprising a first sequence aligning to the reference human genome and a second sequence aligning to the reference genome of the pathogen, thereby identifying Type B human-pathogen chimeric sequence read pairs.

16. The method of claim 15, wherein the predetermined distance is at most 300 bases.

17. The method of claim 15, wherein the identifying the integration breakpoint comprises:
determining a strand orientation of the first sequence read and the second sequence read of each of the Type A human-pathogen chimeric sequence read pairs and the Type B human-pathogen chimeric sequence read pairs;
filtering out, from the Type B human-pathogen chimeric sequence read pairs, Type B human-pathogen chimeric sequence read pairs that have a strand orientation of the first sequence read and the second sequence read inconsistent with the strand orientation of the first sequence read and the second sequence read of a majority of the Type A human-pathogen chimeric sequence read pairs within the human-pathogen candidate integration region; and
after the filtering out, detecting the integration breakpoint based on the Type B human-pathogen chimeric sequence read pairs.

18. The method of claim 15, comprising:
determining a Diversity Score for the Type B human-pathogen chimeric sequence read pairs; wherein the Diversity Score is calculated as $$\frac{\sigma 1 + \sigma 2}{\max\left(\frac{\sigma 1}{\sigma 2}, \frac{\sigma 2}{\sigma 1}\right)},$$

wherein σ1 is a standard deviation of lengths of the first sequences of the Type B human-pathogen chimeric sequence read pairs aligning to the reference human genome, and wherein σ2 is a standard deviation of lengths of the second sequences of the Type B human-pathogen chimeric sequence read pairs aligning to the reference genome of the pathogen; and
detecting the integration breakpoint based on the Type B human-pathogen chimeric sequence read pairs, if the Diversity Score is equal to or higher than a predetermined cutoff value.

19. The method of claim 18, wherein the predetermined cutoff value is at least 4.0.

20. A computer system comprising one or more processors and a non-transitory computer readable medium comprising instructions operable, when executed by the one or more computer processors, to cause the computer system to perform the method of claim 2.

21. A non-transitory computer-readable medium comprising instructions operable, when executed by one or more processors of a computer system, to cause the computer system to perform the method of claim 2.

22. The method of claim 2, further comprising determining a classification of pathology in the organism based at least in part on the pathogen integration.

23. The method of claim 22, wherein the classification of pathology comprises a type of cancer.

24. The method of claim 23, wherein the type of cancer comprises carcinoma of cervix or head and neck squamous cell carcinoma.

* * * * *

UNITED STATES PATENT AND TRADEMARK OFFICE
CERTIFICATE OF CORRECTION

| | |
|---|---|
| PATENT NO. | : 11,447,829 B2 |
| APPLICATION NO. | : 16/456354 |
| DATED | : September 20, 2022 |
| INVENTOR(S) | : Yuk-Ming Dennis Lo et al. |

It is certified that error appears in the above-identified patent and that said Letters Patent is hereby corrected as shown below:

In the Claims

Column 55, Line 45, in the fourth line of Claim 7, delete "add" and replace with --acid--

Column 57, Line 1, in the first line of Claim 18, delete "comprising" and replace with --further comprising--

Signed and Sealed this
Twenty-eighth Day of February, 2023

Katherine Kelly Vidal
*Director of the United States Patent and Trademark Office*